United States Patent
Wexler et al.

(10) Patent No.: US 8,891,817 B2
(45) Date of Patent: Nov. 18, 2014

(54) SYSTEMS AND METHODS FOR AUDIBLY PRESENTING TEXTUAL INFORMATION INCLUDED IN IMAGE DATA

(71) Applicants: Yonatan Wexler, Jerusalem (IL); Amnon Shashua, Mevaseret Zion (IL)

(72) Inventors: Yonatan Wexler, Jerusalem (IL); Amnon Shashua, Mevaseret Zion (IL)

(73) Assignee: OrCam Technologies Ltd., Jerusalem (IL)

( * ) Notice: Subject to any disclaimer, the term of this patent is extended or adjusted under 35 U.S.C. 154(b) by 0 days.

(21) Appl. No.: 14/137,384

(22) Filed: Dec. 20, 2013

(65) Prior Publication Data

US 2014/0270398 A1   Sep. 18, 2014

Related U.S. Application Data

(60) Provisional application No. 61/799,649, filed on Mar. 15, 2013, provisional application No. 61/830,122, filed on Jun. 2, 2013.

(51) Int. Cl.
*G06K 9/00* (2006.01)
*G06K 9/74* (2006.01)

(52) U.S. Cl.
CPC ............. *G06K 17/2765* (2013.01); *G06K 9/74* (2013.01)
USPC ...................................................... 382/100

(58) Field of Classification Search
CPC .................................................... G06F 3/017
USPC ........................................ 382/103, 124–127
See application file for complete search history.

(56) References Cited

U.S. PATENT DOCUMENTS

| | | | | |
|---|---|---|---|---|
| 5,151,945 A | * | 9/1992 | Lee et al. | 382/103 |
| 5,168,531 A | * | 12/1992 | Sigel | 382/291 |
| 6,115,482 A | * | 9/2000 | Sears et al. | 382/114 |
| 2003/0132950 A1 | * | 7/2003 | Surucu et al. | 345/700 |
| 2004/0196400 A1 | * | 10/2004 | Stavely et al. | 348/333.01 |

(Continued)

FOREIGN PATENT DOCUMENTS

| | | |
|---|---|---|
| EP | 2065871 | 6/2009 |
| EP | 2 490 155 A1 | 8/2012 |
| GB | 2 452 124 A | 2/2009 |

OTHER PUBLICATIONS

U.S. Appl. No. 14/136,438, filed Dec. 20, 2013, entitled "Apparatus, Method, and Computer Readable Medium for Expedited Text Reading Using Staged OCR Technique."

(Continued)

*Primary Examiner* — Alex Liew
(74) *Attorney, Agent, or Firm* — Finnegan, Henderson, Farabow, Garrett & Dunner LLP

(57) ABSTRACT

An apparatus and method are provided for identifying and audibly presenting textual information within captured image data. In one implementation, a method is provided for audibly presenting text retrieved from a captured image. According to the method, at least one image of text is received from an image sensor, and the text may include a first portion and a second portion. The method includes identifying contextual information associated with the text, and accessing at least one rule associating the contextual information with at least one portion of text to be excluded from an audible presentation associated with the text. The method further includes performing an analysis on the at least one image to identify the first portion and the second portion, and causing the audible presentation of the first portion.

23 Claims, 24 Drawing Sheets

(56) References Cited

U.S. PATENT DOCUMENTS

| | | |
|---|---|---|
| 2005/0208457 A1 | 9/2005 | Fink et al. |
| 2006/0017810 A1 | 1/2006 | Kurzweil et al. |
| 2012/0212593 A1 | 8/2012 | Na'aman et al. |
| 2013/0169536 A1 | 7/2013 | Wexler et al. |
| 2013/0271584 A1 | 10/2013 | Wexler et al. |

OTHER PUBLICATIONS

U.S. Appl. No. 14/135,727, filed Dec. 20, 2013, entitled "Systems and Method for Audible Facial Recognition."

U.S. Appl. No. 14/131,033, filed Dec. 20, 2013, entitled "Apparatus and Method for Providing Failed-Attempt Feedback Using a Camera on Glasses."

U.S. Appl. No. 14/137,253, filed Dec. 20, 2013, entitled "Apparatus and Method for Executing System Commands Based on Captured Image Data."

U.S. Appl. No. 14/135,757, filed Dec. 20, 2013, entitled "Systems and Methods for Automatic Control of a Continuous Action."

U.S. Appl. No. 14/137,373, filed Dec. 20, 2013, entitled "Apparatus and Method for Automatic Action Selection Based on Image Context."

U.S. Appl. No. 14/135,762, filed Dec. 20, 2013, entitled "Systems and Methods for Performing a Triggered Action."

U.S. Appl. No. 14/137,328, filed Dec. 20, 2013, entitled "Apparatus and Method for Performing Actions Based on Captured Image Data."

U.S. Appl. No. 14/135,859, filed Dec. 20, 2013, entitled "Apparatus Connectable to Glasses."

U.S. Appl. No. 14/137,446, filed Dec. 20, 2013, entitled "Apparatus and Method for Hierarchical Object Identification Using a Camera on Glasses."

U.S. Appl. No. 14/135,928, filed Dec. 20, 2013, entitled "Systems and Methods for Processing Images."

U.S. Appl. No. 14/135,775, filed Dec. 20, 2013, entitled "Systems and Methods for Providing Feedback Based on the State of an Object."

U.S. Appl. No. 14/137,522, filed Dec. 20, 2013, entitled "Apparatus and Method for Using Background Change to Determine Context."

U.S. Appl. No. 14/136,545, filed Dec. 20, 2013, entitled "Apparatus, Method, and Computer Readable Medium for Recognizing Text on a Curved Surface."

U.S. Appl. No. 14/136,876, filed Dec. 20, 2013, entitled "Apparatus and Method for Analyzing Images."

Karacs, Kristof et al., "Bionic Eyeglass: An Audio Guide for Visually Impaired," Biomedical Circuits and Systems Conference, 2006, BIOCAS 2006, IEEE, Piscataway, NJ, Nov. 29, 2006, p. 190-193.

Lai, Chin-Lun et al., "An Integrated Portable Vision Assistant Agency for the Visual Impaired People," 2009 IEEE International Conference on Control and Automation, Christchurch, New Zealand, Dec. 9-11, 2009 (6 pages).

International Search Report and Written Opinion mated by the European Patent Office on Aug. 6 2014, in Internationai Application No. PCT/IB2014/000935 (8 pages).

\* cited by examiner

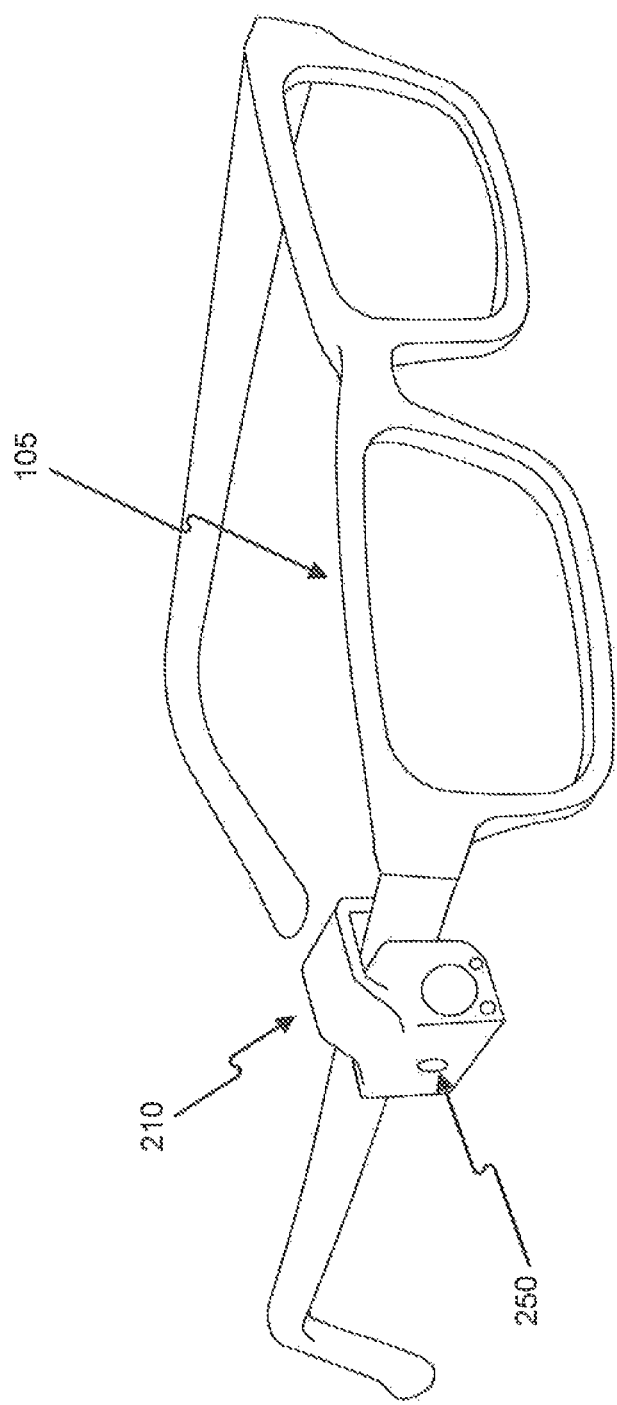

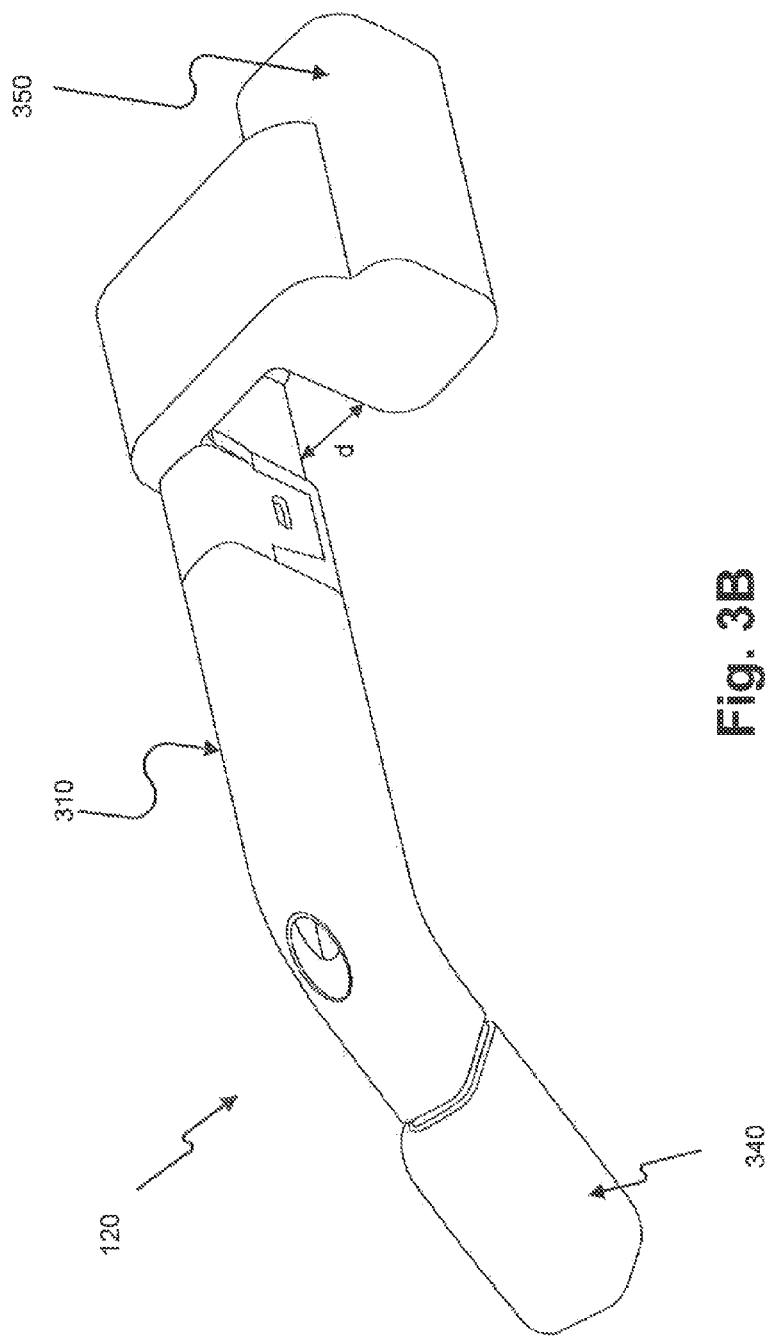

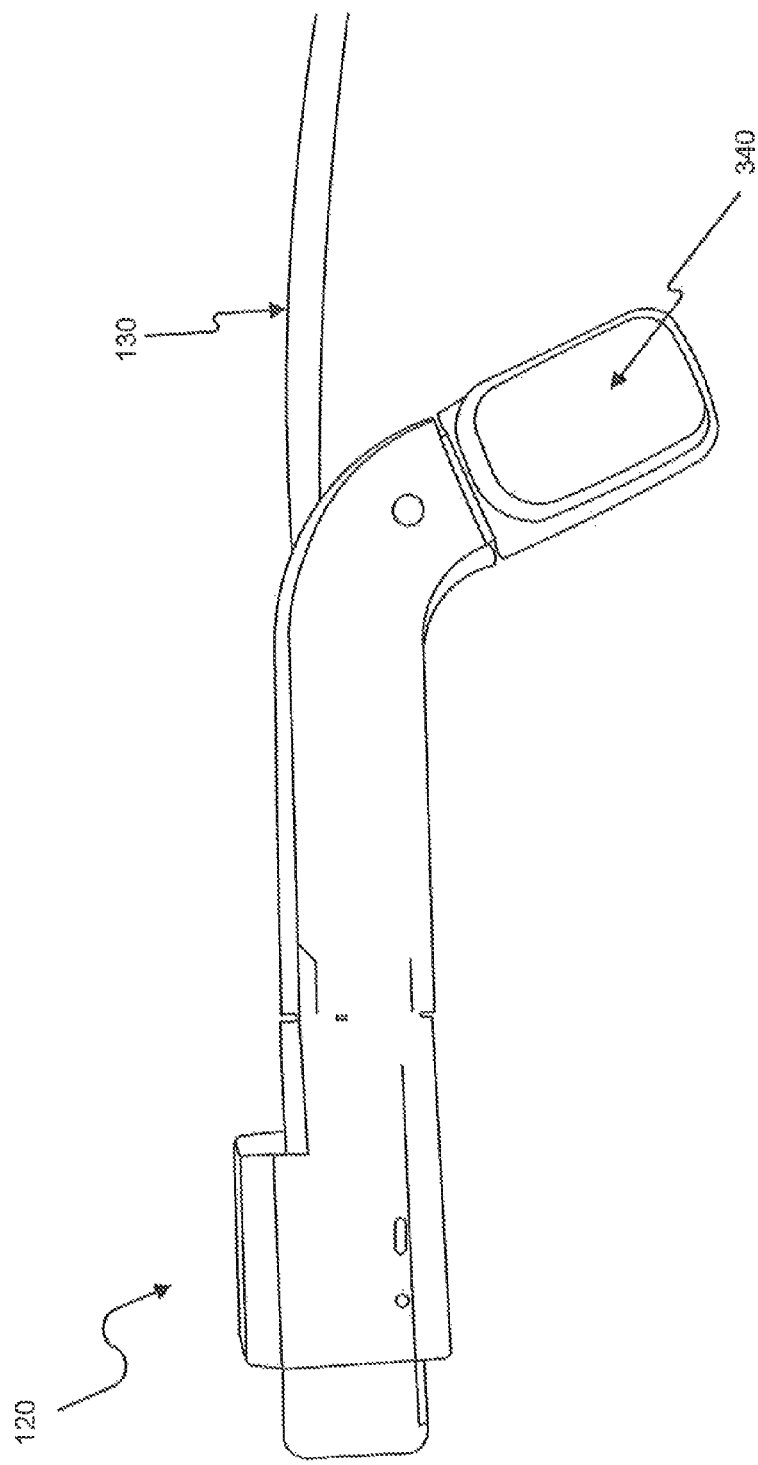

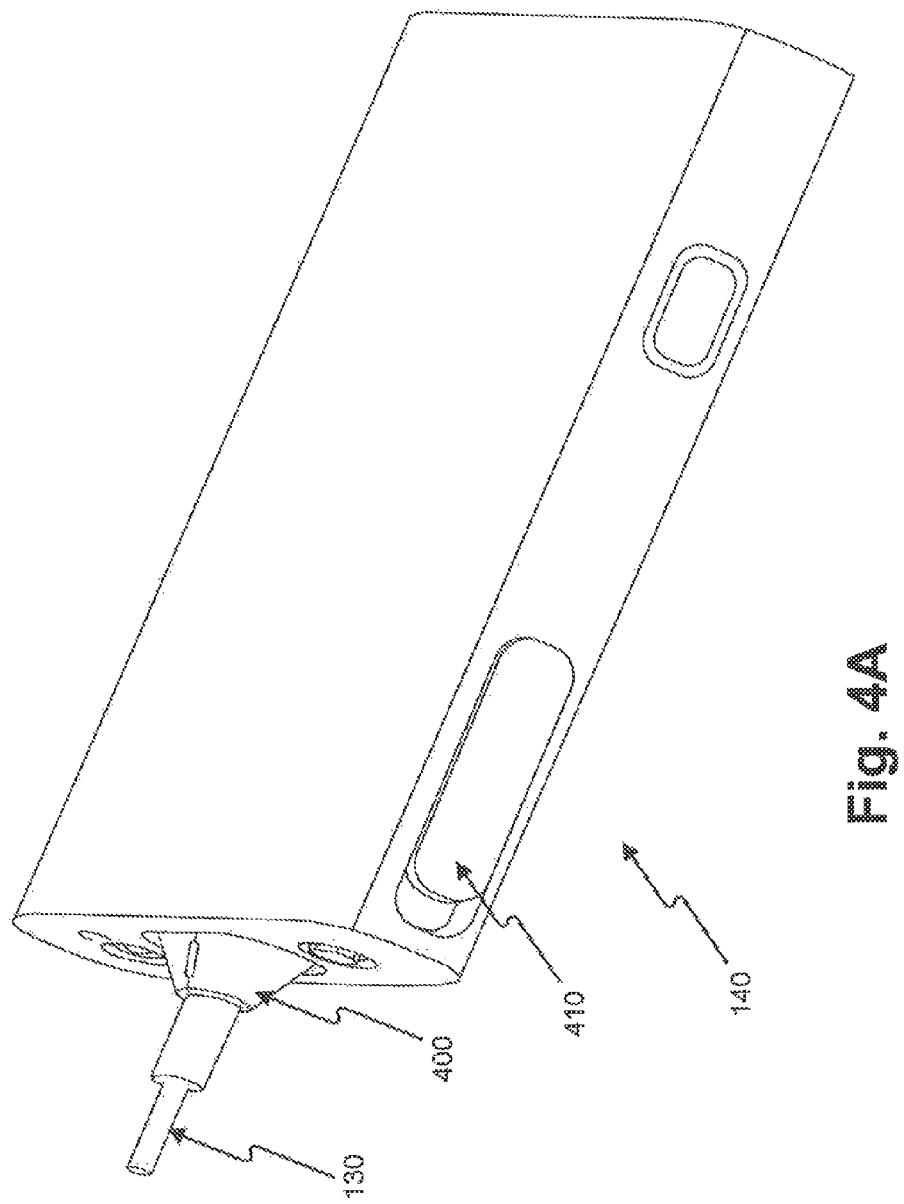

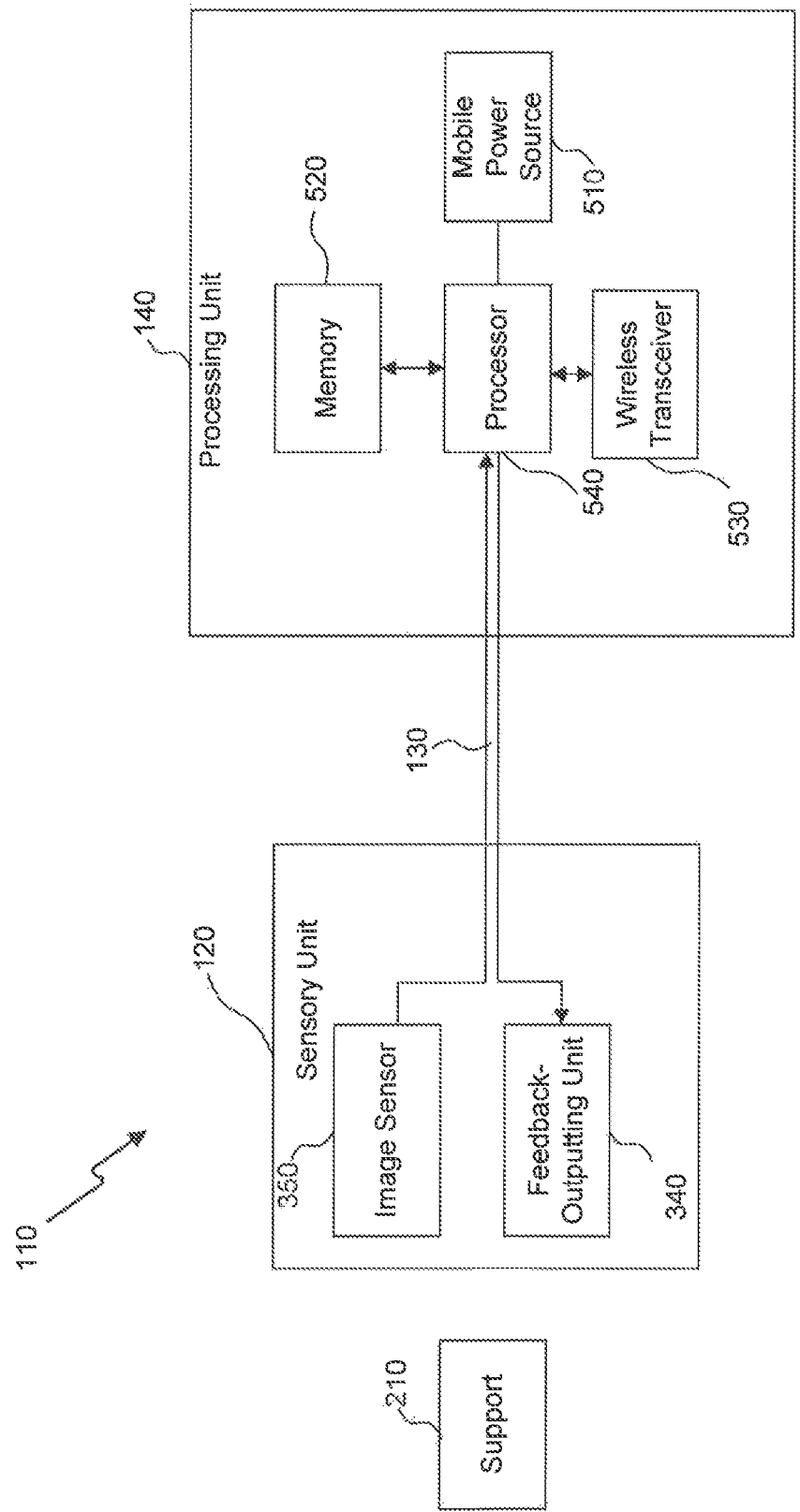

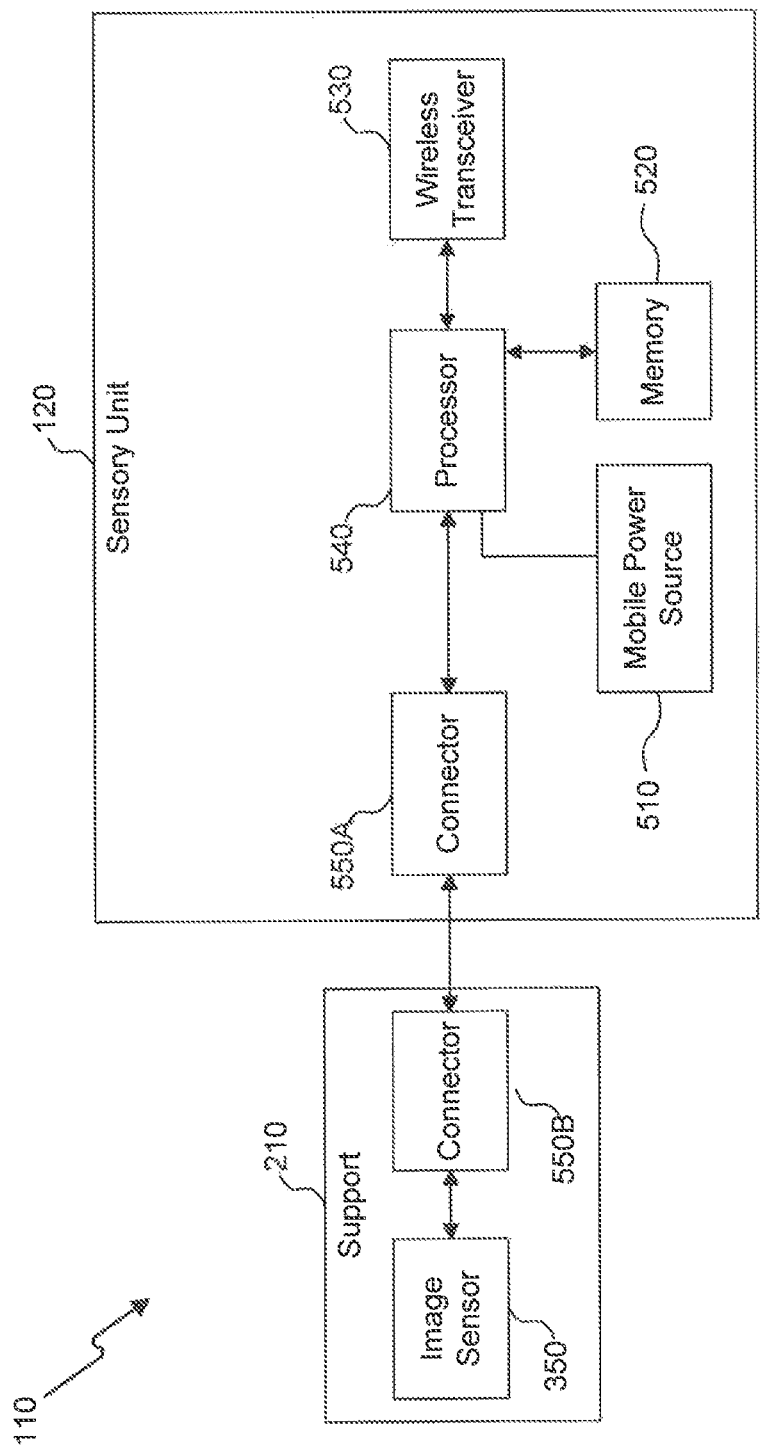

SYSTEMS AND METHODS FOR AUDIBLY PRESENTING TEXTUAL INFORMATION INCLUDED IN IMAGE DATA

CROSS REFERENCE TO RELATED APPLICATIONS

This application claims the benefit of priority of U.S. Provisional Patent Application No. 61/799,649, filed on Mar. 15, 2013, and U.S. Provisional Patent Application No. 61/830,122, filed on Jun. 2, 2013, both of which are incorporated herein by reference in their entirety.

BACKGROUND

I. Technical Field

This disclosure generally relates to devices and methods for providing information to a user. More particularly, this disclosure relates to devices and methods for providing information to a user by processing images captured from the environment of the user.

II. Background Information

Visual acuity is an indication of the clarity or clearness of a person's vision that is commonly measured twenty feet from an object. When measuring visual acuity, the ability of a person to identify black symbols on a white background at twenty feet is compared to the ability of a person with normal eyesight. This comparison can be symbolized by a ratio. For example, a ratio of 20/70 vision means a person located at a distance of twenty feet can see what a person with normal vision can see at seventy feet. A person has low vision if he or she has a visual acuity between 20/70 and 20/200 in the better-seeing eye that cannot be corrected or improved with regular eyeglasses. The prevalence of low vision is about one in a hundred for people in their sixties and rapidly increases to one in five for people in their nineties. Low vision may also depend on the environment. For example, some individuals may be able to see only when there is ample light.

A person may have low vision (also known as visual impairment) for several reasons. Other than eye damage and failure of the brain to receive visual cues sent by the eyes, different medical conditions may cause visual impairment. Medical conditions that may cause visual impairment include Age-related Macular Degeneration (AMD), retinitis pigmentosa, cataract, and diabetic retinopathy.

AMD, which usually affects adults, is caused by damage to the retina that diminishes vision in the center of a person's visual field. The lifetime risk for developing AMD is strongly associated with certain genes. For example, the lifetime risk of developing AMD is 50% for people that have a relative with AMD, versus 12% for people that do not have relatives with AMD.

Retinitis pigmentosa is an inherited, degenerative eye disease that causes severe vision impairment and often blindness. The disease process begins with changes in pigment and damage to the small arteries and blood vessels that supply blood to the retina. There is no cure for retinitis pigmentosa and no known treatment can stop the progressive vision loss caused by the disease.

A cataract is a clouding of the lens inside the eye which leads to a decrease in vision. Over time, a yellow-brown pigment is deposited within the lens and obstructs light from passing and being focused onto the retina at the back of the eye. Biological aging is the most common cause of a cataract, but a wide variety of other risk factors (e.g., excessive tanning, diabetes, prolonged steroid use) can cause a cataract.

Diabetic retinopathy is a systemic disease that affects up to 80% of all patients who have had diabetes for ten years or more. Diabetic retinopathy causes microvascular damage to a blood-retinal barrier in the eye and makes the retinal blood vessels more permeable to fluids.

People with low vision experience difficulties due to lack of visual acuity, field-of-view, color perception, and other visual impairments. These difficulties affect many aspects of everyday life. Persons with low vision may use magnifying glasses to compensate for some aspects of low vision. For example, if the smallest letter a person with 20/100 vision can read is five times larger than the smallest letter that a person with 20/20 vision can read, then 5× magnification should make everything that is resolvable to the person with 20/20 vision resolvable to the person with low vision. However, magnifying glasses are expensive and cannot remedy all aspects of low vision. For example, a person with low vision who wears magnifying glasses may still have a difficult time recognizing details from a distance (e.g., people, signboards, traffic lights, etc.). Accordingly, there is a need for other technologies that can assist people who have low vision accomplish everyday activities.

SUMMARY

Embodiments consistent with the present disclosure provide devices and methods for providing information to a user by processing images captured from the environment of the user. The disclosed embodiments may assist persons who have low vision.

Consistent with disclosed embodiments, a system audibly presents text retrieved from a captured image. In one aspect, the system includes at least one processor device configured to receive at least one image of text to be audibly presented. The text may include a first portion and a second portion. The at least one processor device may be further configured to identify contextual information associated with the text, and access at least one rule associating the contextual information with at least one portion of text to be excluded from an audible presentation associated with the text. The at least one processor device may be further configured to perform an analysis on the at least one image to identify the first portion and the second portion, and cause the audible presentation. The audible presentation may include the first portion and exclude the second portion.

Consistent with disclosed embodiments, a system audibly presents text retrieved from a captured image. In one aspect, the system includes an image sensor configured to capture images from an environment of a user, and at least one processor device configured to receive at least one image of text to be audibly presented. The text may include a first portion and a second portion. The at least one processor device may be further configured to identify contextual information associated with the text, and access at least one rule associating the contextual information with at least one portion of text to be excluded from an audible presentation associated with the text. The at least one processor device may be further configured to perform an analysis on the at least one image to identify the first portion and the second portion, and cause the audible presentation. The audible presentation may include the first portion and exclude the second portion.

Consistent with further disclosed embodiments, a method for audibly presenting text retrieved from a captured image includes receiving at least one image of text to be audibly presented. In one aspect, the text includes a first portion and a second portion. The method further includes identifying contextual information associated with the text, and accessing at least one rule associating the contextual information with at least one portion of text to be excluded from an audible presentation associated with the text. The method further includes performing an analysis on the at least one image to identify the first portion and the second portion, and causing the audible presentation. The audible presentation may include the first portion and exclude the second portion.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 2C is a schematic illustration of the support shown in FIG. 2A mounted on a pair of glasses;

FIG. 4A is a schematic illustration of an example of a processing unit from a first viewpoint;

FIG. 5A is a block diagram illustrating an example of the components of an apparatus for aiding persons who have low vision according to a first embodiment;

FIG. 5C is a block diagram illustrating an example of the components of an apparatus for aiding persons who have low vision according to a third embodiment;

DETAILED DESCRIPTION

Figure 1:
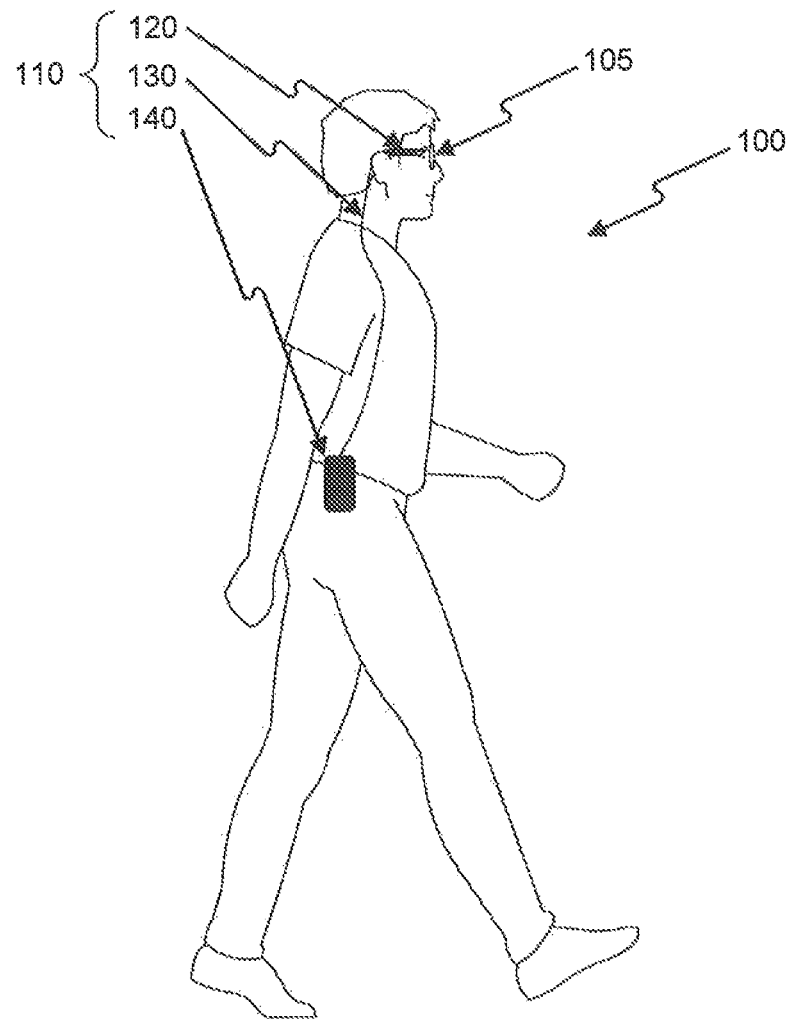
FIG. 1 is a schematic illustration of a user wearing an apparatus for aiding persons who have low vision.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Disclosed embodiments provide devices and methods for assisting people who have low vision. One example of the disclosed embodiments is a device that includes a camera configured to capture real-time image data from the environment of the user. The device also includes a processing unit configured to process the real-time image data and provide real-time feedback to the user. The real-time feedback may include, for example, an output that audibly identifies individuals from a distance, reads signboards, and/or identifies the state of a traffic light, FIG. 1 illustrates a user 100 wearing an apparatus 110 connected to glasses 105, consistent with a disclosed embodiment. Apparatus 110 may provide functionality for aiding user 100 with various daily activities that are otherwise difficult for user 100 to accomplish due to low vision. Glasses 105 may be prescription glasses, magnifying glasses, non-prescription glasses, safety glasses, sunglasses, etc.

As shown in FIG. 1, apparatus 110 includes a sensory unit 120 and a processing unit 140. Sensory unit 120 may be connected to a support (not shown in FIG. 1) that is mounted on glasses 105. In addition, sensory unit 120 may include an image sensor (not shown in FIG. 1) for capturing real-time image data of the field-of-view of user 100. The term "image data" includes any form of data retrieved from optical signals in the near-infrared, infrared, visible, and ultraviolet spectrums. The image data may be used to form video clips and/or photographs.

Processing unit 140 may communicate wirelessly or via a wire 130 connected to sensory unit 120. In some embodiments, processing unit 140 may produce an output of audible feedback to user 100 (e.g., using a speaker or a bone conduction headphone).

Apparatus 110 is one example of a device capable of implementing the functionality of the disclosed embodiments. Other devices capable of implementing the disclosed embodiments include, for example, a mobile computer with a camera (e.g., a smartphone, a smartwatch, a tablet, etc.) or a clip-on-camera configured to communicate with a processing unit (e.g., a smartphone or a dedicated processing unit, which can be carried in a pocket). A person skilled in the art will appreciate that different types of devices and arrangements of devices may implement the functionality of the disclosed embodiments.

Figure 2A:
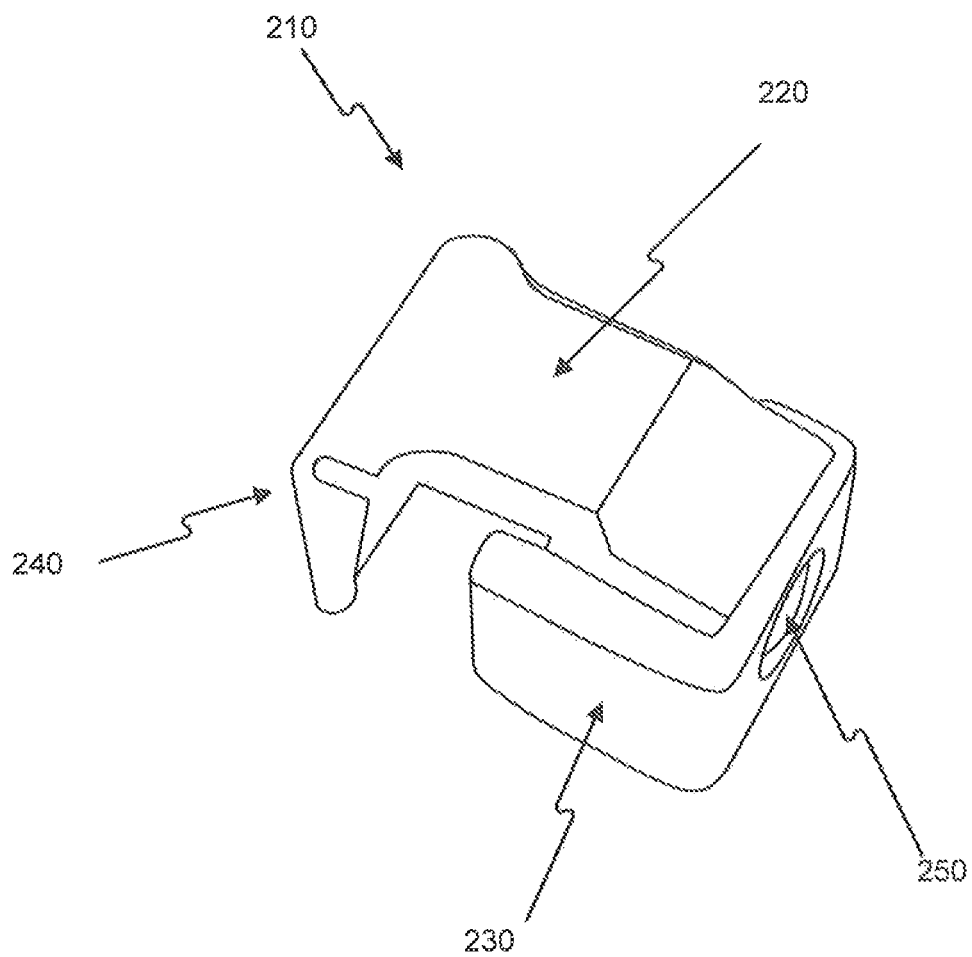
FIG. 2A is a schematic illustration of an example of a support from a first viewpoint.

FIG. 2A is a schematic illustration of an example of a support 210. As discussed in connection with FIG. 1, support 210 may be mounted on glasses 105 and connect to sensory unit 120. The term "support" includes any device or structure that enables detaching and reattaching of a device including a camera to a pair of glasses or to another object (e.g., a helmet). Support 210 may be made from plastic (e.g., polycarbonate), metal e.g., aluminum), or a combination of plastic and metal (e.g., carbon fiber graphite). Support 210 may be mounted on glasses 105 using screws, bolts, snaps, or any fastening means used in the art.

As shown in FIG. 2A, support 210 includes a base 230 connected to a clamp 240. A bridge 220 connects base 230 with clamp 240. Base 230 and clamp 240 enable sensory unit 120 to easily attach to and detach from support 210. In one embodiment, base 230 may include an internally threaded member 250 for cooperating with a screw (not shown in FIG. 2A) to mount support 210 on glasses 105.

Figure 2B:
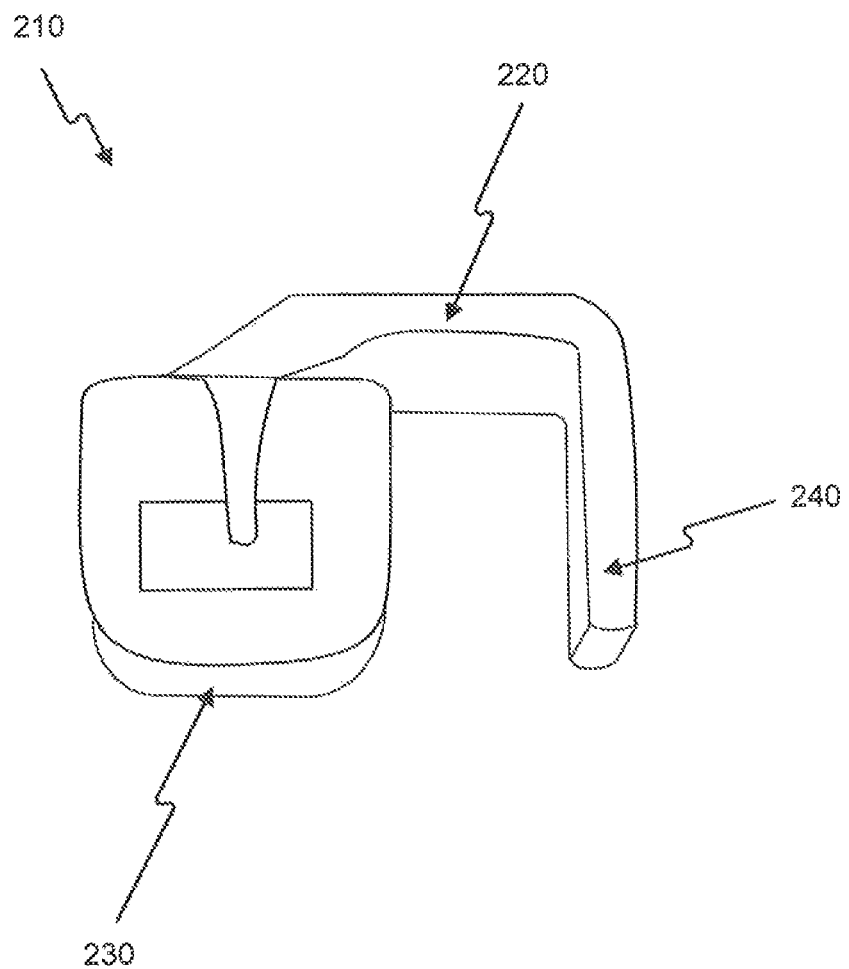
FIG. 2B is a schematic illustration of the support shown in FIG. 2A from a second viewpoint.

FIG. 2B illustrates support 210 from a second viewpoint. The viewpoint shown in FIG. 2B is from a side orientation of support 210.

FIG. 2C illustrates support 210 mounted on glasses 105. Support 210 may be configured for mounting on any kind of glasses (e.g., eyeglasses, sunglasses, 3D glasses, safety glasses, etc.). As shown in FIG. 2C, sensory unit 120 is not attached to support 210 and, accordingly, support 210 may be sold separately from apparatus 110. This arrangement makes apparatus 110 compatible with a variety of glasses. For example, some users may have several pairs of glasses and may wish to mount a support on each pair of glasses.

In other embodiments, support 210 may be an integral part of a pair of glasses, or sold and installed by an optometrist. For example, support 210 may be configured for mounting on the arms of glasses 105 near the frame front, but before the hinge. Alternatively, support 210 may be configured for mounting on the bridge of glasses 105.

Figure 2D:
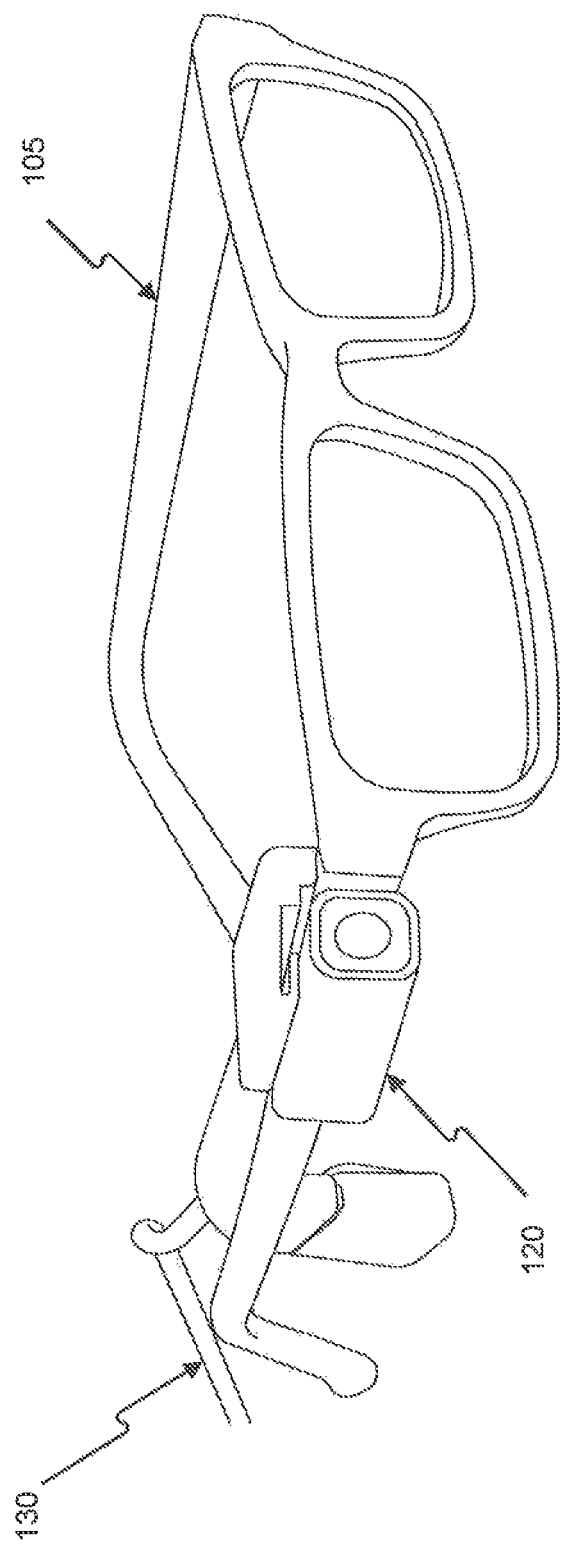
FIG. 2D is a schematic illustration of a sensory unit attached to the support that is mounted on the pair of glasses shown in FIG. 2C.

FIG. 2D illustrates sensory unit 120 attached to support 210 (not visible in FIG. 2D), and support 210 mounted on glasses 105. In some embodiments, support 210 may include a quick release mechanism for disengaging and reengaging sensory unit 120. For example, support 210 and sensory unit 120 may include magnetic elements. As an alternative example, support 210 may include a male latch member and sensory unit 120 may include a female receptacle.

When sensory unit 120 is attached (or reattached) to support 210, the field-of-view of a camera associated with sensory unit 120 may be substantially identical to the field-of-view of user 100. Accordingly, in some embodiments, after support 210 is attached to sensory unit 120, directional calibration of sensory unit 120 may not be required because sensory unit 120 aligns with the field-of-view of user 100.

In other embodiments, support 210 may include an adjustment component (not shown in FIG. 2D) to enable calibration of the aiming direction of sensory unit 120 in a substantially set position that is customized to user 100 wearing glasses 105. For example, the adjustment component may include an adjustable hinge to enable vertical and horizontal alignment of the aiming direction of sensory unit 120. Adjusting the alignment of sensory unit 120 may assist users who have a unique and individual visual impairment. The adjustment may be internal or external to sensory unit 120.

Figure 2E:
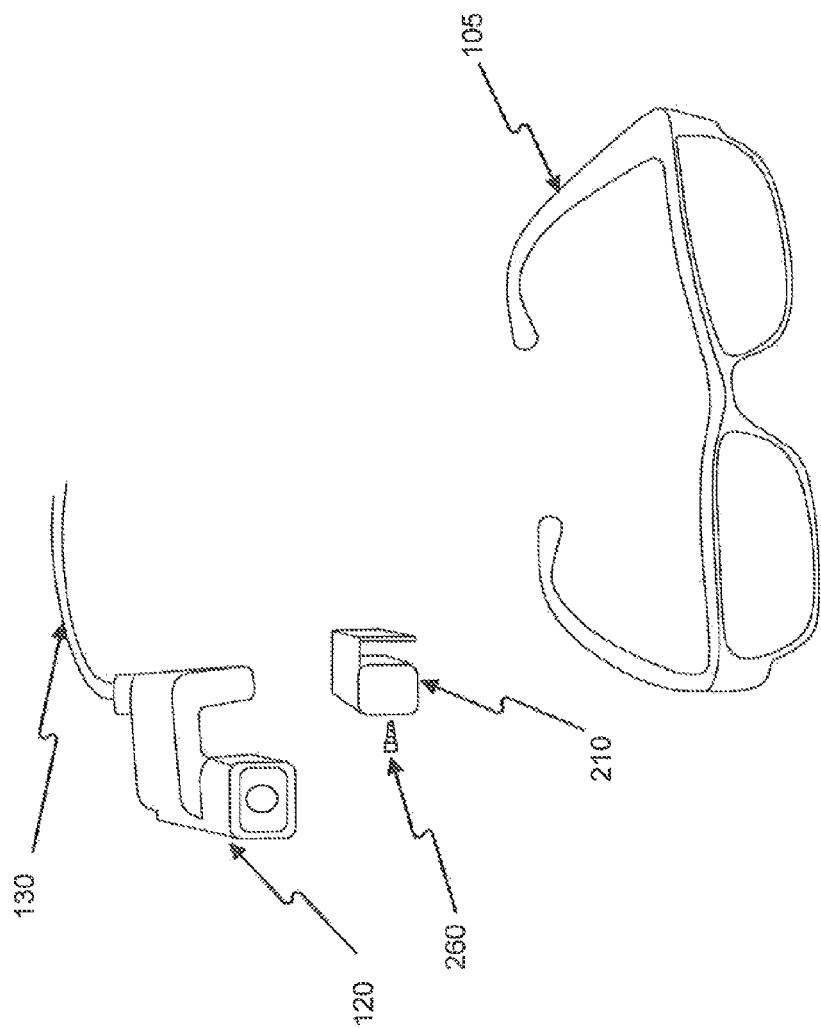
FIG. 2E is an exploded view of FIG. 2D.

FIG. 2E is an exploded view of the components shown in FIG. 2D. Sensory unit 120 may be attached to glasses 105 in the following way. Initially, support 210 may be mounted on glasses 105 using screw 260. Next, screw 260 may be inserted into internally threaded member 250 (not shown in FIG. 2E) in the side of support 210. Sensory unit 120 may then be clipped on support 210 such that it is aligned with the field-of-view of user 100.

Figure 3A:
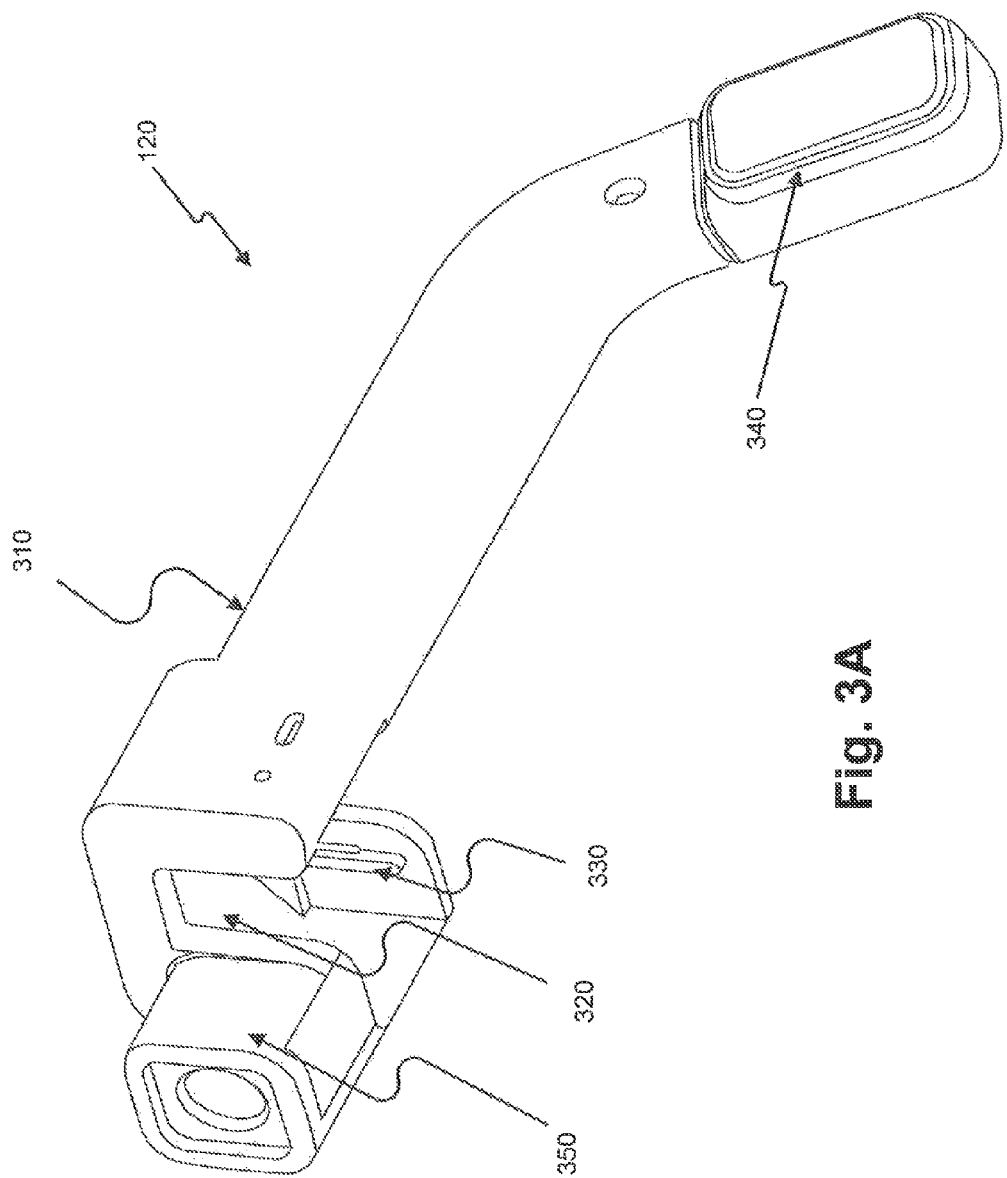
FIG. 3A is a schematic illustration of an example of a sensory unit from a first viewpoint.

FIG. 3A is a schematic illustration of sensory unit 120 from a first viewpoint. As shown in FIG. 3A, sensory unit 120 includes a feedback-outputting unit 340 and an image sensor 350.

Sensory unit 120 is configured to cooperate with support 210 using clip 330 and groove 320, which fits the dimensions of support 210. The term "sensory unit" refers to any electronic device configured to capture real-time images and provide a non-visual output. Furthermore, as discussed above, sensory unit 120 includes feedback-outputting unit 340. The term "feedback-outputting unit" includes any device configured to provide information to a user.

In some embodiments, feedback-outputting unit 340 may be configured to be used by blind persons and persons with low vision. Accordingly, feedback-outputting unit 340 may be configured to output nonvisual feedback. The term "feedback" refers to any output or information provided in response to processing at least one image in an environment. For example, feedback may include a descriptor of a branded product, an audible tone, a tactile response, and/or information previously recorded by user 100. Furthermore, feedback-outputting unit 340 may comprise appropriate components for outputting acoustical and tactile feedback that people with low vision can interpret. For example, feedback-outputting unit 340 may comprise audio headphones, a speaker, a bone conduction headphone, interfaces that provide tactile cues, vibrotactile stimulators, etc.

As discussed above, sensory unit 120 includes image sensor 350. The term "image sensor" refers to a device capable of detecting and converting optical signals in the near-infrared, infrared, visible, and ultraviolet spectrums into electrical signals. The electric signals may be used to form an image based on the detected signal. For example, image sensor 350 may be part of a camera. In some embodiments, when sensory unit 120 is attached to support 210, image sensor 350 may acquire a set aiming direction without the need for directional calibration. The set aiming direction of image sensor 350 may substantially coincide with the field-of-view of user 100 wearing glasses 105. For example, a camera associated with image sensor 350 may be installed within sensory unit 120 in a predetermined angle in a position facing slightly downwards (e.g., 5-15 degrees from the horizon). Accordingly, the set aiming direction of image sensor 350 may match the field-of-view of user 100.

As shown in FIG. 3A, feedback-outputting unit 340 and image sensor 350 are included in a housing 310. The term "housing" refers to any structure that at least partially covers, protects, or encloses a sensory unit. The housing may be made from one or more different materials (e.g., plastic or aluminum). In one embodiment, housing 310 may be designed to engage with a specific pair of glasses having a specific support (e.g., support 210). In an alternative embodiment, housing 310 may be designed to engage more than one pair of glasses, each having a support (e.g., support 210) mounted thereon. Housing 310 may include a connector for receiving power from an external mobile-power-source or an internal mobile-power-source, and for providing an electrical connection to image sensor 350.

FIG. 3B is a schematic illustration of sensory unit 120 from a second viewpoint. As shown in FIG. 3B, housing 310 includes a U-shaped element. An inner distance "d" between each side of the U-shaped element is larger than the width of the arm of glasses 105. Additionally, the inner distance "d" between each side of the U-shaped element is substantially equal to a width of support 210. The inner distance "d" between each side of the U-shaped element may allow user 100 to easily attach housing 310 to support 210, which may be mounted on glasses 105. As illustrated in FIG. 3B, image sensor 350 is located on one side of the U-shaped element and feedback-outputting unit 340 is located on another side of the U-shaped element.

Figure 3C:
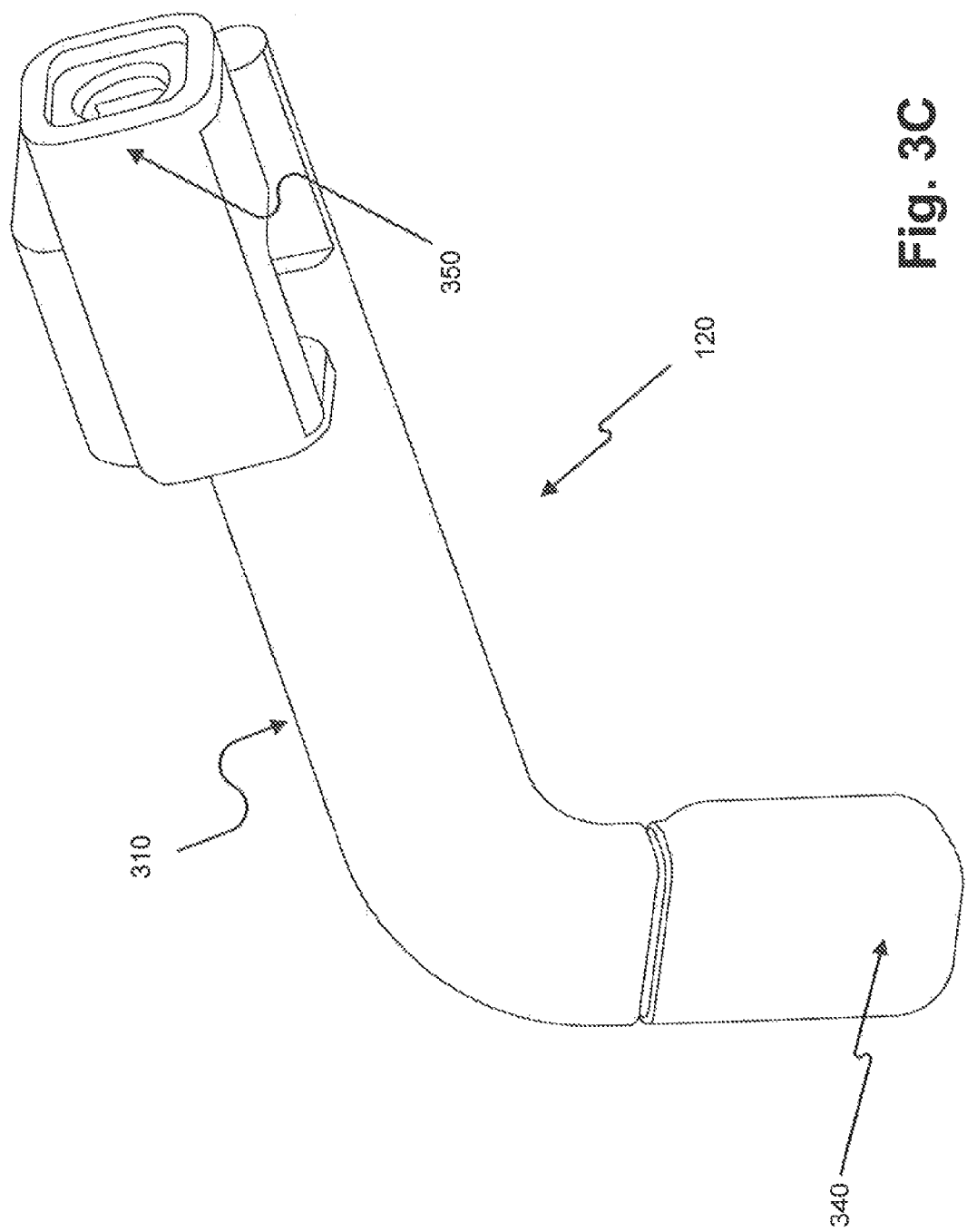
FIG. 3B is a schematic illustration of the sensory unit shown in FIG. 3A from a second viewpoint.
FIG. 3O is a schematic illustration of the sensory unit shown in FIG. 3A from a third viewpoint.
FIG. 3D is a schematic illustration of the sensory unit shown in FIG. 3A from a fourth viewpoint.
FIG. 3E is a schematic illustration of the sensory unit shown in FIG. 3A in an extended position.

FIG. 3C is a schematic illustration of sensory unit 120 from a third viewpoint. The viewpoint shown in FIG. 3C is from a side orientation of sensory unit 120 and shows the side of the U-shaped element that includes image sensor 350.

FIG. 3D is a schematic illustration of sensory unit 120 from a fourth viewpoint. The viewpoint shown in FIG. 3D is from an opposite side of the orientation shown in FIG. 3C, FIG. 3D shows the side of the U-shaped element that includes feedback-outputting unit 340.

Figure 3E:
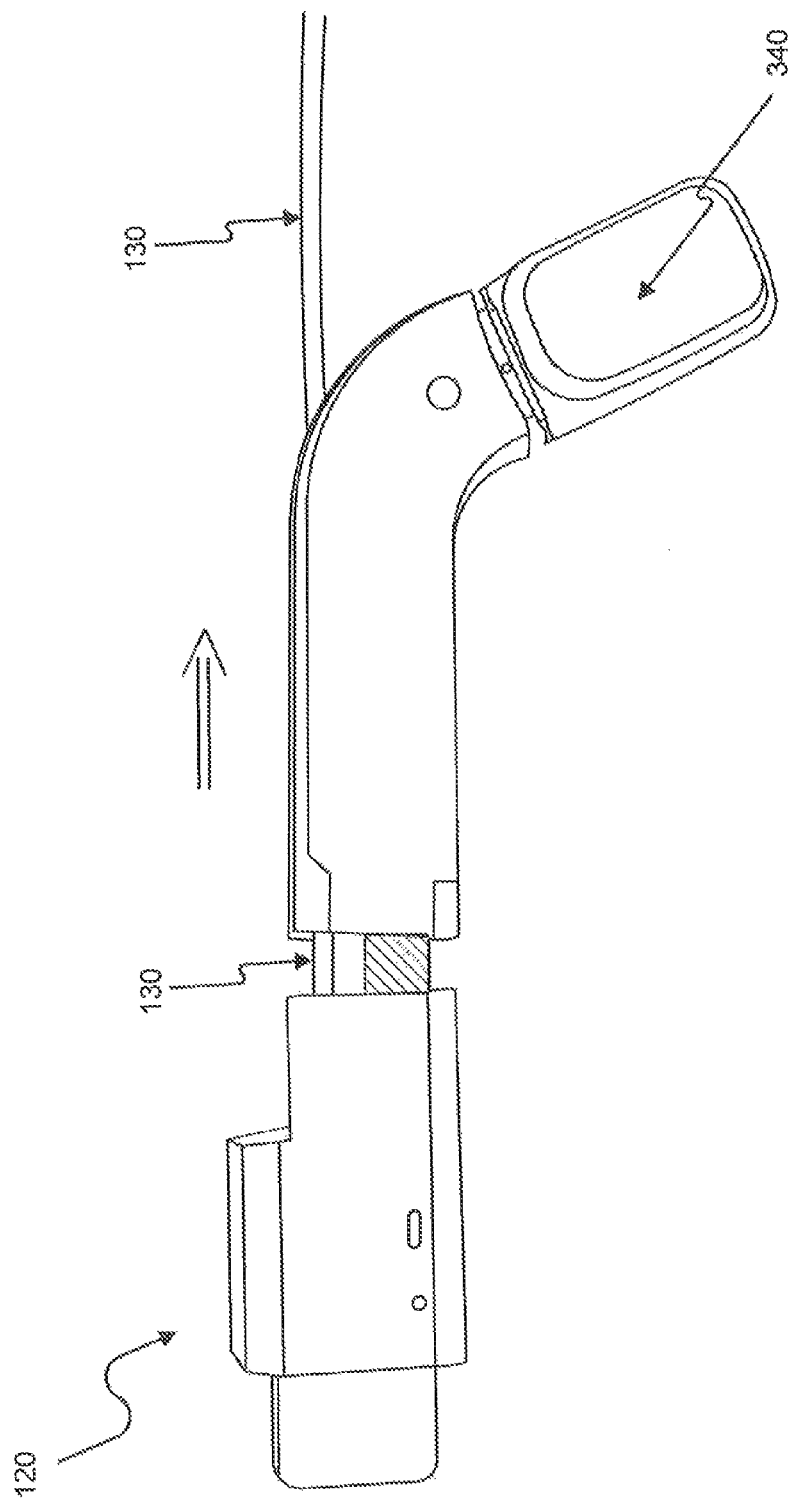

FIG. 3E is a schematic illustration of the sensory unit shown in FIG. 3A in an extended position. As shown in FIG. 3E, a portion of sensory unit 120 is extendable and wire 130 may pass through a channel of sensory unit 120. This arrangement may allow a user to adjust the length and the angle of sensory unit 120 without interfering with the operation of apparatus 110.

User 100 may adjust the U-shaped element of sensory unit 120 so that feedback-outputting unit 340 is positioned adjacent to the user's ear or the user's temple. Accordingly, sensory unit 120 may be adjusted for use with different users who may have different head sizes. Alternatively, a portion of sensory unit 120 may be flexible such that the angle of feedback-outputting unit 340 is relative to the user's ear or the user's temple.

FIG. 4A is a schematic illustration of processing unit 140. As shown in FIG. 4A, processing unit 140 has a rectangular shape, which easily fits in a pocket of user 100. Processing unit 140 includes a connector 400 for connecting wire 130 to processing unit 140. Wire 130 may be used to transmit power from processing unit 140 to sensory unit 120, and data to and from processing unit 140 to sensory unit 120. Alternatively, wire 130 may comprise multiple wires (e.g., a wire dedicated to power transmission and a wire dedicated to data transmission).

Processing unit 140 includes a function button 410 for enabling user 100 to provide input to apparatus 110. Function button 410 may accept different types of tactile input (e.g., a tap, a click, a double-click, a long press, a right-to-left slide, a left-to-right slide). In some embodiments, each type of input may be associated with a different action. For example, a tap may be associated with the function of confirming an action, while a right-to-left slide may be associated with the function of repeating the last output.

Figure 4B:
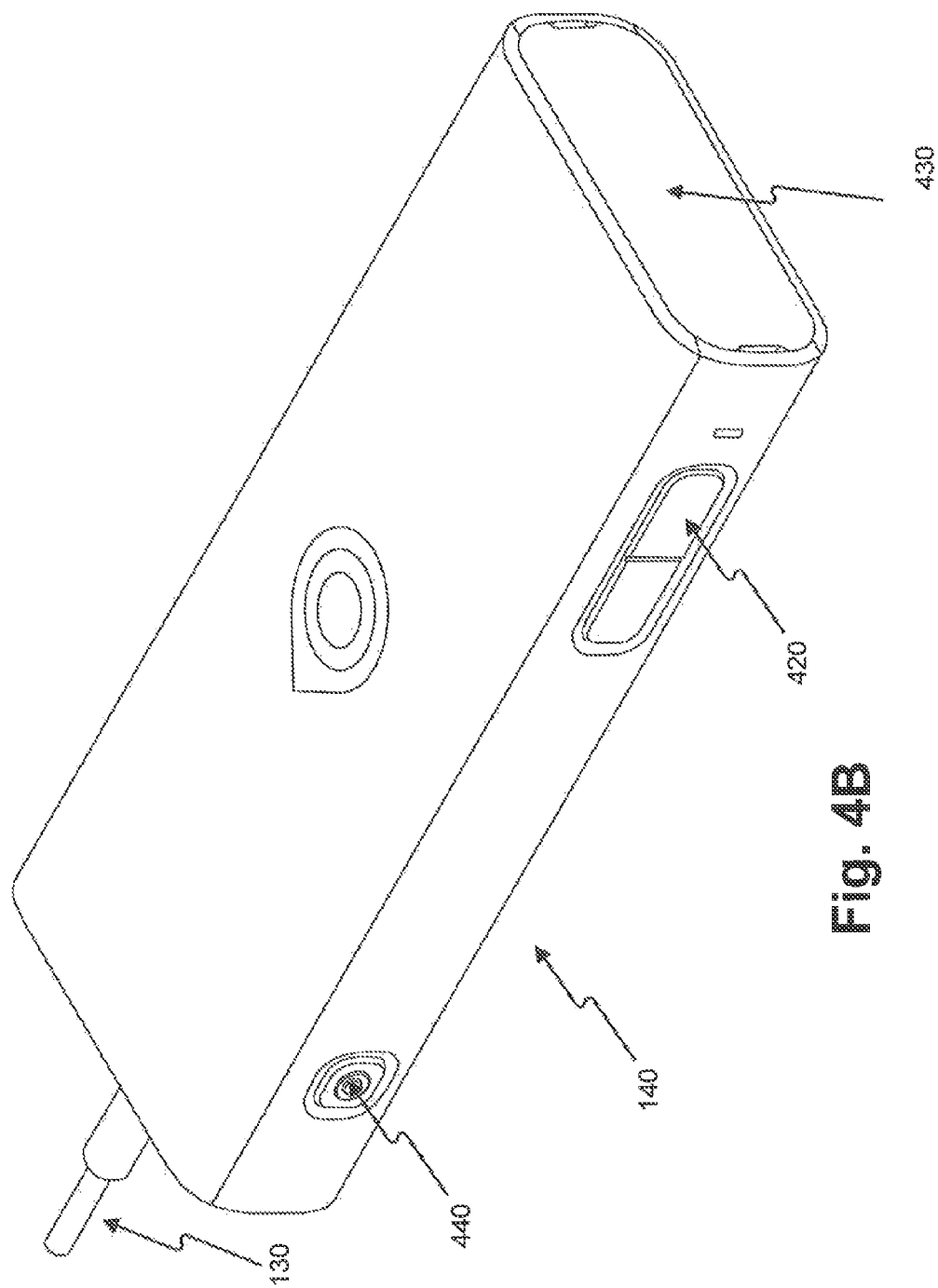
FIG. 4B is a schematic illustration of the processing unit shown in FIG. 4A from a second viewpoint.

FIG. 4B is a schematic illustration of processing unit 140 from a second viewpoint. As shown in FIG. 4B, processing unit 140 includes a volume switch 420, a battery pack compartment 430, and a power port 440. In one embodiment, user 100 may charge apparatus 110 using a charger connectable to power port 440. Alternatively, user 100 may replace a battery pack (not shown) stored in battery pack compartment 430.

FIG. 5A is a block diagram illustrating the components of apparatus 110 according to a first embodiment. Specifically, FIG. 5A depicts an embodiment in which apparatus 110 comprises sensory unit 120 and processing unit 140, as discussed in connection with, for example, FIG. 1. Furthermore, sensory unit 120 may be physically coupled to support 210.

As shown in FIG. 5A, sensory unit 120 includes feedback-outputting unit 340 and image sensor 350. Although one image sensor is depicted in FIG. 5A, sensory unit 120 may include a plurality of image sensors (e.g., two image sensors). For example, in an arrangement with more than one image sensor, each of the image sensors may be face a different direction or be associated with a different camera (e.g., a wide angle camera, a narrow angle camera, an IR camera, etc.). In other embodiments (not shown in the figure) sensory unit 120 may also include buttons and other sensors such as a microphone and inertial measurements devices.

As further shown in FIG. 5A, sensory unit 120 is connected to processing unit 140 via wire 130. Processing unit 140 includes a mobile power source 510, a memory 520, a wireless transceiver 530, and a processor 540.

Processor 540 may constitute any physical device having an electric circuit that performs a logic operation on input or inputs. For example, processor 540 may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by processor 540 may, for example, be pre-loaded into a memory integrated with or embedded into processor 540 or may be stored in a separate memory (e.g., memory 520). Memory 520 may comprise a Random Access Memory (RAM), a Read-Only Memory (ROM), a hard disk, an optical disk, a magnetic medium, a flash memory, other permanent, fixed, or volatile memory, or any other mechanism capable of storing instructions.

Although one processor is shown in FIG. 5A, processing unit 140 may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

In some embodiments, processor 540 may change the aiming direction of image sensor 350 using image data provided from image sensor 350. For example, processor 540 may recognize that a user is reading a book and determine that the aiming direction of image sensor 350 is offset from the text. That is, because the words in the beginning of each line of text are not fully in view, processor 540 may determine that image sensor 350 is tilted down and to the right. Responsive thereto, processor 540 may adjust the aiming direction of image sensor 350.

Processor 540 may access memory 520. Memory 520 may be configured to store information specific to user 100. For example, data for image representations of known individuals, favorite products, personal items, etc., may be stored in memory 520. In one embodiment, user 100 may have more than one pair of glasses, with each pair of glasses having support 210 mounted thereon. Accordingly, memory 520 may store information (e.g., personal settings) associated with each pair of glasses. For example, when a user wears his sunglasses may have different preferences than when the user wears reading glasses.

As shown in FIG. 5A, processing unit 140 includes mobile power source 510. Mobile power source 510 may be configured to power processing unit 140 and/or sensory unit 120. The term "mobile power source" includes any device capable of providing electrical power, which can be easily carried by a hand (e.g., the total weight of mobile power source 510 may be less than a pound). Thus, the mobility of the power source enables user 100 to use apparatus 110 in a variety of situations. For example, mobile power source 510 may include one or more batteries (e.g., nickel-cadmium batteries, nickel-metal hydride batteries, and lithium-ion batteries) or any other type of electrical power supply. In some embodiments, mobile power source 510 may be rechargeable and contained within a casing that holds processing unit 140. In other embodiments, mobile power source 510 may include one or more energy harvesting devices for converting ambient energy into electrical energy (e.g., portable solar power units, human vibration units, etc.).

Apparatus 110 may operate in a low-power-consumption mode and in a processing-power-consumption mode. For example, mobile power source 510 can produce five hours of processing-power-consumption mode and fifteen hours of low-power-consumption mode. Accordingly, different power consumption modes may allow mobile power source 510 to produce sufficient power for powering processing unit 140 for various time periods (e.g., more than two hours, more than four hours, more than ten hours, etc.).

Mobile power source 510 may power one or more wireless transceivers (e.g., wireless transceiver 530 in FIG. 5A). The term "wireless transceiver" refers to any device configured to exchange transmissions over an air interface by use of radio frequency, infrared frequency, magnetic field, or electric field. Wireless transceiver 530 may use any known standard to transmit and/or receive data (e.g., Wi-Fi, Bluetooth®, Bluetooth Smart, 802.15.4, or ZigBee). In some embodiments, wireless transceiver 530 may transmit data (e.g., raw image data or audio data) from image sensor 350 to processing unit 140, or wireless transceiver 530 may transmit data from processing unit 140 to feedback-outputting unit 340.

In another embodiment, wireless transceiver 530 may communicate with a different device (e.g., a hearing aid, the user's smartphone, or any wirelessly controlled device) in the environment of user 100. For example, wireless transceiver 530 may communicate with an elevator using a Bluetooth® controller. In such an arrangement, apparatus 110 may recognize that user 100 is approaching an elevator and call the elevator, thereby minimizing wait time. In another example, wireless transceiver 530 may communicate with a smart TV. In such an arrangement, apparatus 110 may recognize that user 100 is watching television and identify specific hand movements as commands for the smart TV (e.g., switching channels). In yet another example, wireless transceiver 530 may communicate with a virtual cane. A virtual cane is any device that uses a laser beam or ultrasound waves to determine the distance from user 100 to an object.

Figure 5B:
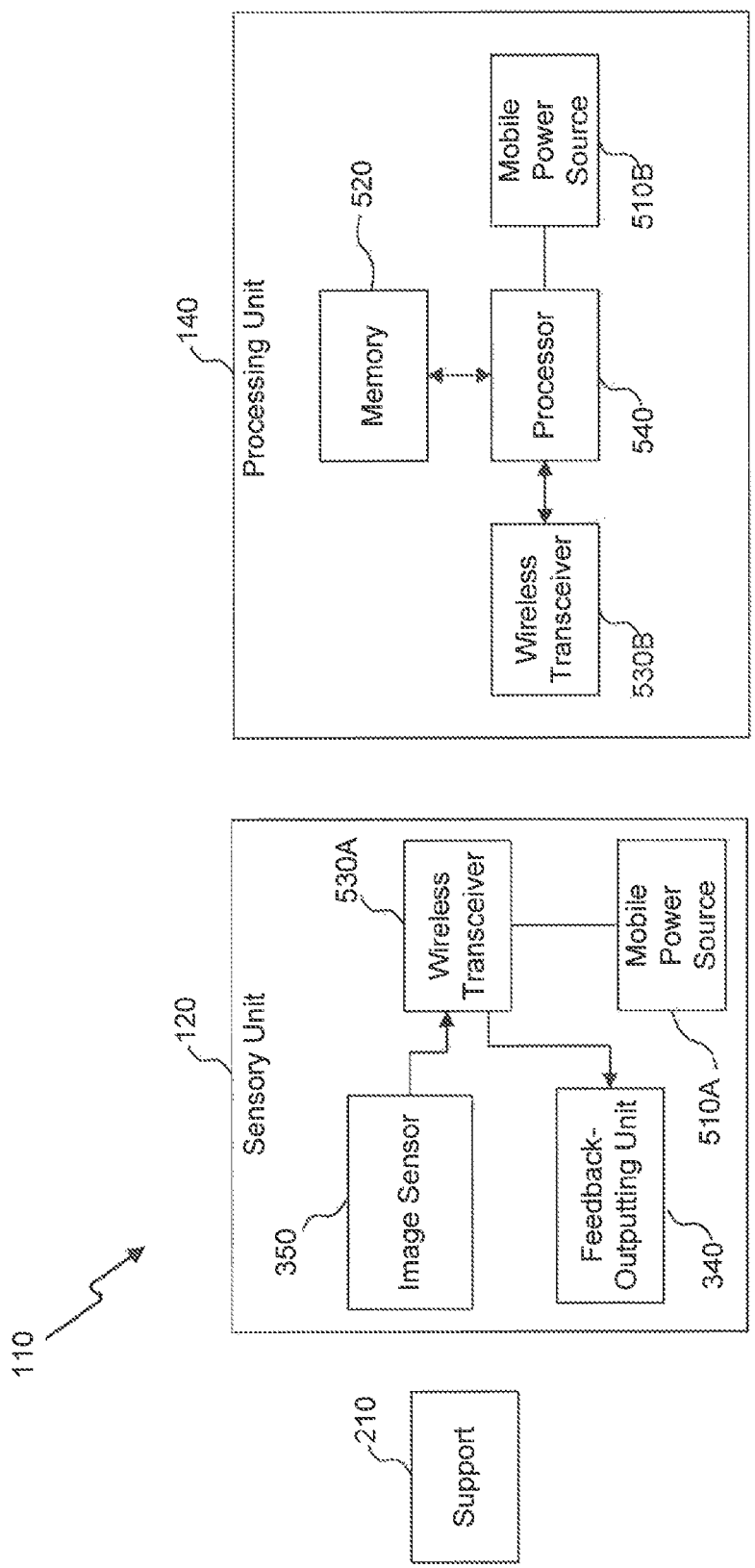
FIG. 5B is a block diagram illustrating an example of the components of an apparatus for aiding persons who have low vision according to a second embodiment.

FIG. 5B is a block diagram illustrating the components of apparatus 110 according to a second embodiment. In FIG. 5B, similar to the arrangement shown in FIG. 5A, support 210 is used to couple sensory unit 120 to a pair of glasses. However, in the embodiment shown in FIG. 5B, sensory unit 120 and processing unit 140 communicate wirelessly. For example, wireless transceiver 530A can transmit image data to processing unit 140 and receive information to be outputted via feedback-outputting unit 340.

In this embodiment, sensory unit 120 includes feedback-outputting unit 340, mobile power source 510A, wireless transceiver 530A, and image sensor 350. Mobile power source 510A is contained within sensory unit 120. As further shown in FIG. 5B, processing unit 140 includes wireless transceiver 530B, processor 540, mobile power source 510B, and memory 520.

FIG. 5C is a block diagram illustrating the components of apparatus 110 according to a third embodiment. In particular, FIG. 5C depicts an embodiment in which support 210 includes image sensor 350 and connector 550B. In this embodiment, sensory unit 120 provides functionality for processing data and, therefore, a separate processing unit is not needed in such a configuration.

As shown in FIG. 5C, sensory unit 120 includes processor 540, connector 550A, mobile power source 510, memory 520, and wireless transceiver 530. In this embodiment, apparatus 110 does not include a feedback-outputting unit. Accordingly, wireless transceiver 530 may communicate directly with a hearing aid (e.g., a Bluetooth® hearing aid). In addition, in this embodiment, image sensor 350 is included in support 210. Accordingly, when support 210 is initially mounted on glasses 105, image sensor 350 may acquire a set aiming direction. For example, a camera associated with image sensor 350 may be installed within support 210 in a predetermined angle in a position facing slightly downwards (e.g., 7-12 degrees from the horizon). Furthermore, connector 550A and connector 550B may allow data and power to be transmitted between support 210 and sensory unit 120.

Figure 5D:
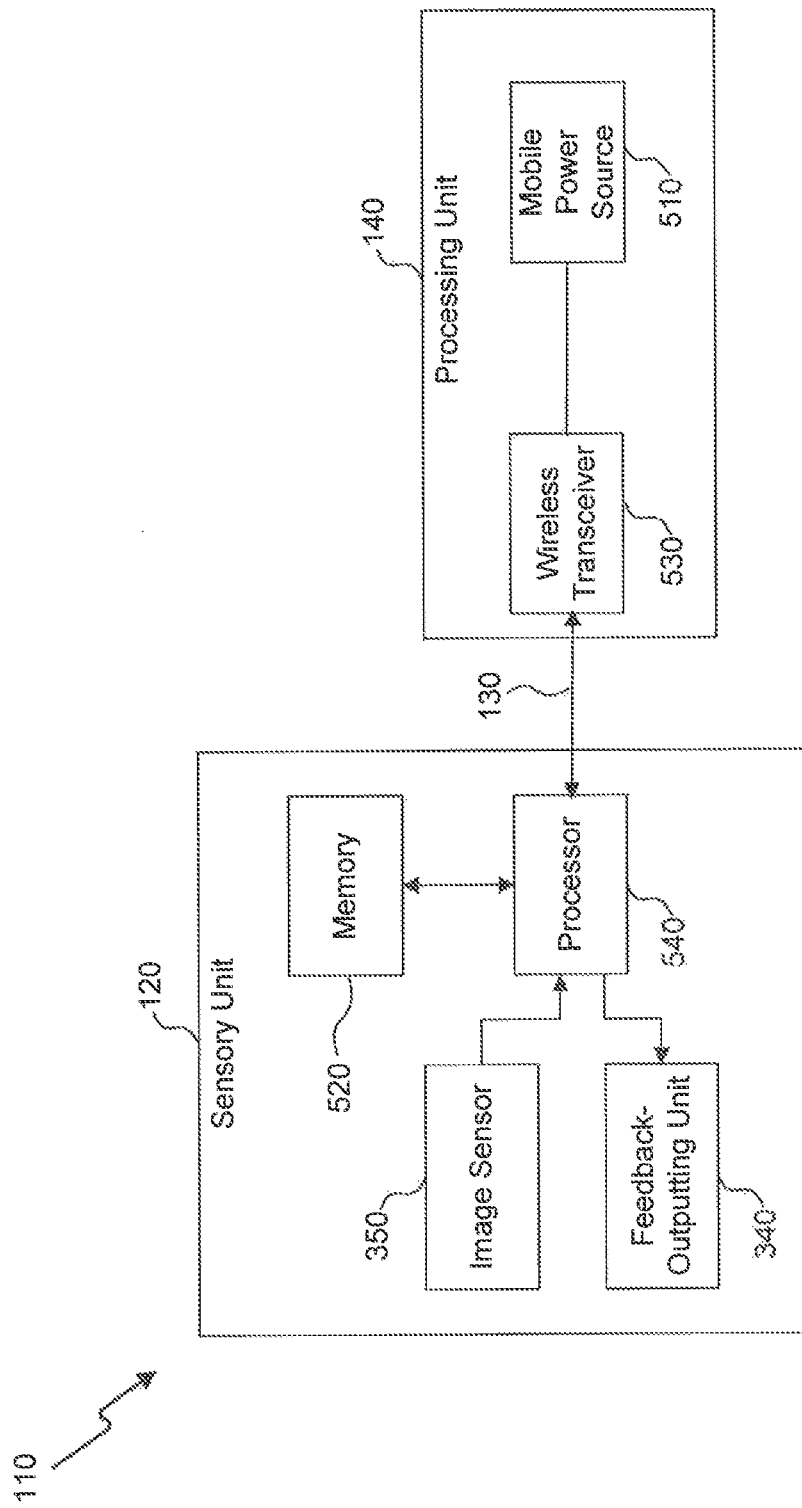
FIG. 5D is a block diagram illustrating an example of the components of an apparatus for aiding persons who have low vision according to a fourth embodiment.

FIG. 5O is a block diagram illustrating the components of apparatus 110 according to a fourth embodiment. In FIG. 5D, sensory unit 120 couples directly to a pair of glasses without the need of a support. In this embodiment, sensory unit 120 includes image sensor 350, feedback-outputting unit 340, processor 540, and memory 520. As shown in FIG. 5D, sensory unit 120 is connected via a wire 130 to processing unit 140. Additionally, in this embodiment, processing unit 140 includes mobile power source 510 and wireless transceiver 530.

As will be appreciated by a person skilled in the art having the benefit of this disclosure, numerous variations and/or modifications may be made to the disclosed embodiments. Not all components are essential for the operation of apparatus 110. Any component may be located in any appropriate part of apparatus 110 and the components may be rearranged into a variety of configurations while providing the functionality of the disclosed embodiments. Therefore, the foregoing configurations are examples and, regardless of the configurations discussed above, apparatus 110 can assist persons who have low vision with their everyday activities in numerous ways.

One way apparatus 110 can assist persons who have low vision is by identifying relevant objects in an environment. For example, in some embodiments, processor 540 may execute one or more computer algorithms and/or signal-processing techniques to find objects relevant to user 100 in image data captured by sensory unit 120. The term "object" refers to any physical object, person, text, or surroundings in an environment.

In one embodiment, apparatus 110 can perform a hierarchical object identification process. In a hierarchical object identification process, apparatus 110 can identify objects from different categories (e.g., spatial guidance, warning of risks, objects to be identified, text to be read, scene identification, and text in the wild) of image data. For example, apparatus 110 can perform a first search in the image data to identify objects from a first category, and after initiating the first search, execute a second search in the image data to identify objects from a second category.

In another embodiment, apparatus 110 can provide information associated with one or more of the objects identified in image data. For example, apparatus 110 can provide information such as the name of an individual standing in front of user 100. The information may be retrieved from a dynamic database stored in memory 520. If the database does not contain specific information associated with the object, apparatus 110 may provide user 100 with nonvisual feedback indicating that a search was made, but the requested information was not found in the database. Alternatively, apparatus 110 may use wireless transceiver 530 to search for and retrieve information associated with the object from a remote database (e.g., over a cellular network or Wi-Fi connection to the Internet).

Another way apparatus 110 can assist persons who have low vision is by performing a continuous action that relates to an object in an environment. A continuous action may involve providing continuous feedback regarding the object. For example, apparatus 110 can provide continuous feedback associated with an object identified within a field-of-view of image sensor 350, and suspend the continuous feedback when the object moves outside the field-of-view of image sensor 350. Examples of continuous feedback may include audibly reading text, playing a media file, etc. In addition, in some embodiments, apparatus 110 may provide continuous feedback to user 100 based on information derived from a discrete image or based on information derived from one or more images captured by sensory unit 120 from the environment of user 100.

Another type of continuous action includes monitoring the state of an object in an environment. For example, in one embodiment, apparatus 110 can track an object as long as the object remains substantially within the field-of-view of image sensor 350. Furthermore, before providing user 100 with feedback, apparatus 110 may determine whether the object is likely to change its state. If apparatus 110 determines that the object is unlikely to change its state, apparatus 110 may provide a first feedback to user 100. For example, if user 100 points to a road sign, apparatus 110 may provide a first feedback that comprises a descriptor of the road sign. However, if apparatus 110 determines that the object is likely to change its state, apparatus 110 may provide a second feedback to user 100 after the object has changed its state. For example, if user 100 points at a traffic light, the first feedback may comprise a descriptor of the current state of the traffic light (e.g., the traffic light is red) and the second feedback may comprise a descriptor indicating that the state of traffic light has changed (i.e., the traffic light is now green).

Apparatus 110 may also determine that an object that is expected to change its state is not functioning and provide appropriate feedback. For example, apparatus 110 may provide a descriptor indicating that a traffic light is broken.

Apparatus 110 can also assist persons who have low vision by making intelligent decisions regarding a person's intentions. Apparatus 110 can make these decisions by understanding the context of a situation. Accordingly, disclosed embodiments may retrieve contextual information from captured image data and adjust the operation of apparatus 110 based on at least the contextual information. The term "contextual information" (or "context") refers to any information having a direct or indirect relationship with an object in an environment. In some embodiments, apparatus 110 may retrieve different types of contextual information from captured image data. One type of contextual information is the time and/or the place that an image of the object was captured. Another example of a type of contextual information is the meaning of text written on the object. Other examples of types of contextual information include the identity of an object, the type of the object, the background of the object, the location of the object in the frame, the physical location of the user relative to the object, etc.

In an embodiment, the type of contextual information that is used to adjust the operation of apparatus 110 may vary based on objects identified in the image data and/or the particular user who wears apparatus 110. For example, when apparatus 110 identifies a package of cookies as an object, apparatus 110 may use the location of the package (i.e., at home or at the grocery store) to determine whether or not to read the list of ingredients aloud. Alternatively, when apparatus 110 identifies a signboard identifying arrival times for trains as an object, the location of the sign may not be relevant, but the time that the image was captured may affect the output. For example, if a train is arriving soon, apparatus 110 may read aloud the information regarding the coming train. Accordingly, apparatus 110 may provide different responses depending on contextual information.

Apparatus 110 may use contextual information to determine a processing action to execute or an image resolution of image sensor 350. For example, after identifying the existence of an object, contextual information may be used to determine if the identity of the object should be announced, if text written on the object should be audibly read, if the state of the object should be monitored, or if an image representation of the object should be saved. In some embodiments, apparatus 110 may monitor a plurality of images and obtain contextual information from specific portions of an environment. For example, motionless portions of an environment may provide background information that can be used to identify moving objects in the foreground.

Yet another way apparatus 110 can assist persons who have low vision is by automatically carrying out processing actions after identifying specific objects and/or hand gestures in the field-of-view of image sensor 350. For example, processor 540 may execute several actions after identifying one or more triggers in image data captured by apparatus 110. The term "trigger" includes any information in the image data that may cause apparatus 110 to execute an action. For example, apparatus 110 may detect as a trigger a finger of user 100 pointing to one or more coins. The detection of this gesture may cause apparatus 110 to calculate a sum of the value of the one or more coins. As another example of a trigger, an appearance of an individual wearing a specific uniform (e.g., a policeman, a fireman, a nurse) in the field-of-view of image sensor 350 may cause apparatus 110 to make an audible indication that this particular individual is nearby.

In some embodiments, the trigger identified in the image data may constitute a hand-related trigger. The term "hand-related trigger" refers to a gesture made by, for example, the user's hand, the user's finger, or any pointed object that user 100 can hold (e.g., a cane, a wand, a stick, a rod, etc.).

In other embodiments, the trigger identified in the image data may include an erratic movement of an object caused by user 100. For example, unusual movement of an object can trigger apparatus 110 to take a picture of the object. In addition, each type of trigger may be associated with a different action. For example, when user 100 points to text, apparatus 110 may audibly read the text. As another example, when user 100 erratically moves an object, apparatus 110 may audibly identify the object or store the representation of that object for later identification.

Apparatus 110 may use the same trigger to execute several actions. For example, when user 100 points to text, apparatus 110 may audibly read the text. As another example, when user 100 points to a traffic light, apparatus 110 may monitor the state of the traffic light. As yet another example, when user 100 points to a branded product, apparatus 110 may audibly identify the branded product. Furthermore, in embodiments in which the same trigger is used for executing several actions, apparatus 110 may determine which action to execute based on contextual information retrieved from the image data. In the examples above, wherein the same trigger (pointing to an object) is used, apparatus 110 may use the type of the object (text, a traffic light, a branded product) to determine which action to execute.

To assist user 100 throughout his or her daily activities, apparatus 100 may follow several procedures for saving processing resources and prolonging battery life. For example, apparatus 110 can use several image resolutions to form images. Higher image resolution provides more detailed images, but requires more processing resources. Lower image resolution provides less detailed images, but saves processing resources. Therefore, to prolong battery life, apparatus 110 may have rules for capturing and processing high resolution image under certain circumstances, and rules for capturing and processing low resolution image when possible. For example, apparatus 110 may capture higher resolution images when performing Optical Character Recognition (OCR), and capture low resolution images when searching for a trigger.

One of the common challenges persons with low vision face on a daily basis is reading. Apparatus 110 can assist persons who have low vision by audibly reading text that is present in user 100 environment. Apparatus 110 may capture an image that includes text using sensory unit 120. After capturing the image, to save resources and to process portions of the text that are relevant to user 100, apparatus 110 may initially perform a layout analysis on the text. The term "layout analysis" refers to any process of identifying regions in an image that includes text. For example, layout analysis may detect paragraphs, blocks, zones, logos, titles, captions, footnotes, etc.

In one embodiment, apparatus 110 can select which parts of the image to process, thereby saving processing resources and battery life. For example, apparatus 110 can perform a layout analysis on image data taken at a resolution of one megapixel to identify specific areas of interest within the text. Subsequently, apparatus 110 can instruct image sensor 350 to capture image data at a resolution of five megapixels to recognize the text in the identified areas. In other embodiments, the layout analysis may include initiating at least a partial OCR process on the text.

In another embodiment, apparatus 110 may detect a trigger that identifies a portion of text that is located a distance from a level break in the text. A level break in the text represents any discontinuity of the text (e.g., a beginning of a sentence, a beginning of a paragraph, a beginning of a page, etc.). Detecting this trigger may cause apparatus 110 to read the text aloud from the level break associated with the trigger. For example, user 100 can point to a specific paragraph in a newspaper and apparatus 110 may audibly read the text from the beginning of the paragraph instead of from the beginning of the page.

In addition, apparatus 110 may identify contextual information associated with text and cause the audible presentation of one portion of the text and exclude other portions of the text. For example, when pointing to a food product, apparatus 110 may audibly identify the calorie value of the food product. In other embodiments, contextual information may enable apparatus 110 to construct a specific feedback based on at least data stored in memory 520. For example, the specific feedback may assist user 100 to fill out a form (e.g., by providing user 100 audible instructions and details relevant to a form in the user's field-of-view).

To improve the audible reading capabilities of apparatus 110, processor 540 may use OCR techniques. The term "optical character recognition" includes any method executable by a processor to retrieve machine-editable text from images of text, pictures, graphics, etc. OCR techniques and other document recognition technology typically use a pattern matching process to compare the parts of an image to sample characters on a pixel-by-pixel basis. This process, however, does not work well when encountering new fonts, and when the image is not sharp. Accordingly, apparatus 110 may use an OCR technique that compares a plurality of sets of image regions that are proximate to each other. Apparatus 110 may recognize characters in the image based on statistics relate to the plurality of the sets of image regions. By using the statistics of the plurality of sets of image regions, apparatus 110 can recognize small font characters defined by more than four pixels e.g., six or more pixels. In addition, apparatus 110 may use several images from different perspectives to recognize text on a curved surface. In another embodiment, apparatus 110 can identify in image data an existence of printed information associated with a system command stored in a database and execute the system command thereafter. Examples of a system command include: "enter training mode," "enter airplane mode," "backup content," "update operating system," etc.

The disclosed OCR techniques may be implemented on various devices and systems and are not limited to use with apparatus 110. For example, the disclosed OCR techniques provide accelerated machine reading of text. In one embodiment, a system is provided for audibly presenting a first part of a text from an image, while recognizing a subsequent part of the text. Accordingly, the subsequent part may be presented immediately upon completion of the presentation of the first part, resulting in a continuous audible presentation of standard text in less than two seconds after initiating OCR.

As is evident from the foregoing, apparatus 110 may provide a wide range of functionality. More specifically, in embodiments consistent with the present disclosure, apparatus 110 may capture image data that includes textual information and non-textual information disposed within a field-of-view of sensory unit 120, and identify portions of the textual information for audible presentation based on contextual information and one or more contextual rules. Apparatus 110 may use the one or more contextual rules to associate the contextual information with portions of the textual information to include and/or exclude from the audible presentation.

In certain aspects, "textual information" consistent with the disclosed embodiments may include, but is not limited to, printed text, handwritten text, coded text, text projected onto a corresponding surface, text displayed to the user through a corresponding display screen or touchscreen, and any additional or alternate textual information appropriate to the user and to apparatus 110. Further, the "non-textual information" may include, but is not limited to, images of various triggers (e.g., a human appendage, a cane, or a pointer), images of physical objects, images of persons, images of surroundings, and images of other non-textual objects disposed within the field-of-view of sensory unit 120.

Further, in some aspects, "portions" of textual information consistent with the disclosed embodiments may represent one or more linguistic elements capable of conveying literal or practical meaning to the user of apparatus 110. By way of example, such linguistic elements may include, but are not limited to, words, phrases, sentences, paragraphs, and other linguistic elements appropriate to the user and the textual information. The disclosed embodiments are, however, not limited such exemplary linguistic elements, and in further embodiments, portions of textual information consistent with the disclosed embodiments may include numbers, alpha-numeric character strings (e.g., acronyms, license plate numbers, road numbers, etc.), and other structured, non-linguistic elements capable of conveying meaning to the user of apparatus 110.

In certain embodiments, the portions of textual information may be disposed within discrete regions of the captured image data. By of example, the discrete regions may correspond to "zones" within an object associated with the captured image data (e.g., a document or physical object disposed within a field-of-view of sensory unit 120). In certain aspects, textual information disposed within a corresponding one of the zones may be associated with a particular logical role or purpose within the underlying object. For example, sensory unit 120 may capture an image of a train schedule, and the captured image data may include textual information disposed within discrete zones that inform the user of apparatus 110 of departing trains, arriving trains, and general announcements.

In some aspects, "contextual information" may include any information having a direct or indirect relationship with textual or non-textual information disposed within a field-of-view of sensory unit 120 of apparatus 110. By way of example, contextual information consistent with the disclosed embodiments may include, but is not limited to, a time or a location at which apparatus 110 captured a portion of textual and/or non-textual information, information identifying a type of document associated with captured image data (e.g., a newspaper, magazine, or web page), information indicative of one or more user preferences for an audible presentation of textual information, a location of a user, and any additional or alternate contextual information appropriate to the user, the textual information, and apparatus 110.

Further, in some aspects, "contextual rules" consistent with the disclosed embodiments may associate elements of contextual information with elements of textual information to be excluded from an audible presentation of the textual information. By way of example, apparatus 110 may capture image data corresponding to a newspaper article, and the textual information may include text associated with a body of the article, a title of the article, and further, an author, publication date, and page number associated with the article. In such an instance, a contextual rule consistent with the disclosed embodiments may specify that apparatus 110 exclude text corresponding to the author, the publication date, and/or the page number from an audible presentation of the newspaper article.

The disclosed embodiments are, however, not limited to contextual rules that exclude certain portions of textual information from audible presentation. In certain aspects, at least one of the contextual rules may associate elements of the contextual information with one of more of the portions that should be included within the audible presentation. Additionally or alternatively, contextual rules consistent with the disclosed embodiments may specify a presentation order for corresponding portions of textual information, and additionally or alternatively, may specify that one or more portions of the textual information are prioritized during audible presentation.

By way of example, apparatus 110 may capture image data corresponding to a product displayed for sale in a grocery store, and the textual information may include a list of ingredients. In such instances, contextual information associated with the ingredients may identify a food allergy of a corresponding user (e.g., an allergy to peanuts and products processed in proximity to peanuts), and contextual rules consistent with the disclosed embodiments may specify that apparatus 110 prioritize the audible presentation of any ingredients within the list that correspond to the user's food allergy.

Figure 6:
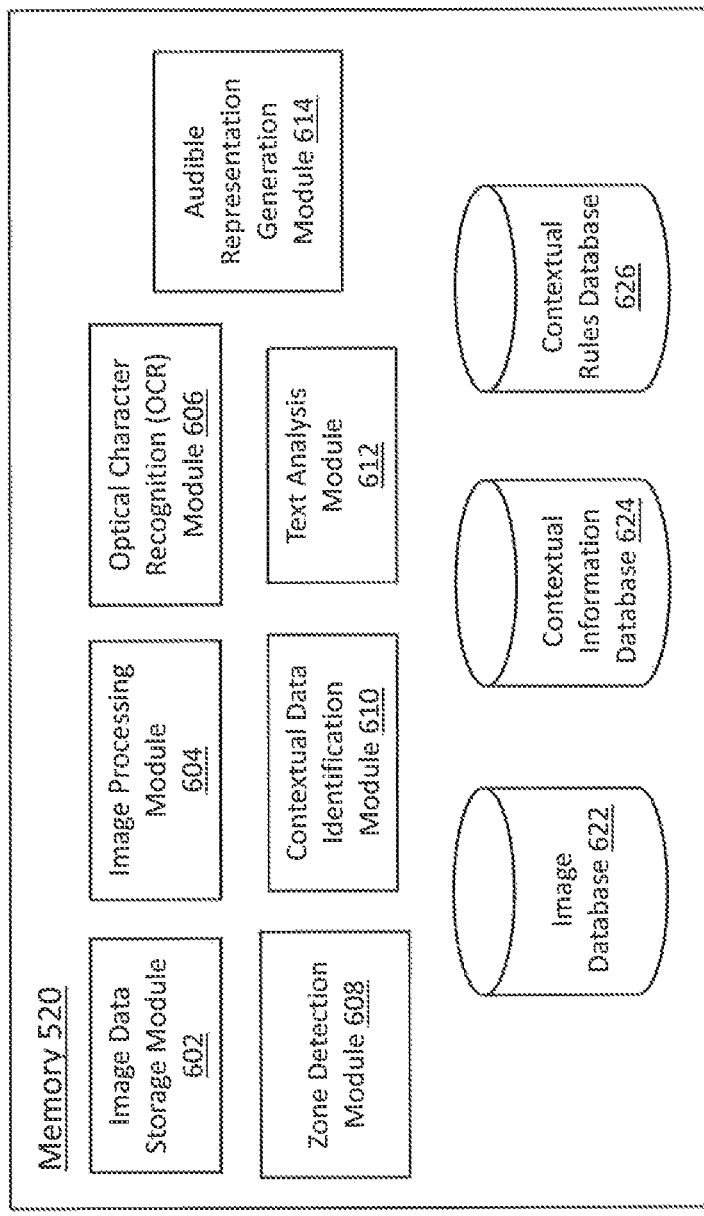
FIG. 6 illustrates an exemplary set of application modules and databases, according to disclosed embodiments.

In an embodiment, apparatus 110 may include a memory (e.g., memory 520) configured to store one or more applications and application modules that, when executed by a processor (e.g., processor 540), enable processor 540 to identify and audible present portions of captured textual data based on corresponding contextual information and one or more contextual rules that associate the contextual information with excluded, included, ordered, or prioritized portions of the textual information. In certain aspects, memory 520 may also be configured to store information that identifies one or more elements of contextual information associated with the captured image data and/or textual information disposed within the captured data. Additionally, memory 520 may store information that identifies one or more contextual rules that associate elements of the contextual information with corresponding portions of the textual information to be excluded, included, ordered, or prioritized within the audible presentation. FIG. 6 illustrates an exemplary structure of memory 520, in accordance with disclosed embodiments.

In FIG. 6, memory 520 may be configured to store an image data storage module 602 and an image database 622. In one embodiment, image data storage module 602, upon execution by processor 540, may enable processor 540 to receive data corresponding to one or more images captured by sensory unit 120, and to store the captured image data within image database 622. In some aspects, the captured image data may include textual information (e.g., printed, handwritten, coded, projected, and/or displayed text) and non-textual information (e.g., images of physical objects, persons, and/or triggers), and processor 540 may store the image data in image database 622 with additional data specifying a time and/or date at which sensory unit 120 captured the image data. In additional embodiments, image data storage module 602 may further enable processor 540 to configure wireless transceiver 530 to transmit the captured image data to one or more devices (e.g., an external data repository or a user's mobile device) in communication with apparatus 110 across a corresponding wired or wireless network.

Memory 520 may also be configured to store an image processing module 604, optical character recognition (OCR) module 606, and a zone detection module 608. In an embodiment, image processing module 604, upon execution by processor 540, may enable processor 540 to process the captured image data and identify textual information within the captured image data. In certain aspects, textual information consistent with the disclosed embodiments may include, but is not limited to, printed text (e.g., text disposed on a page of a newspaper, magazine, book), handwritten text, coded text, text displayed to a user through a display unit of a corresponding device (e.g., an electronic book, a television a web page, or an screen of a mobile application), text disposed on a flat or curved surface of an object within a field-of-view of apparatus 110 (e.g., a billboard sign, a street sign, text displayed on product packaging), text projected onto a corresponding screen (e.g., during presentation of a movie at a theater), and any additional or alternate text disposed within images captured by sensory unit 120.

In an embodiment, OCR module 606 may, upon execution by processor 540, enable processor 540 to perform one or more OCR processes on textual information disposed within the captured image data. By way of example, processor 540 may execute image processing module 604 to identify portions of the captured image data that include textual information, and further, may execute OCR module 606 to retrieve machine-readable text from the textual information. In certain aspects, processor 540 may execute OCR module 606 to identify and retrieve machine-readable text from textual information that includes characters defined by 10 or less pixels, and additionally or alternatively characters defined by 6 or less pixels In further embodiments, zone detection module 608 may, upon execution by processor 540, enable processor 540 to analyze textual information within the captured data to detect one or more "zones" of textual information. In certain aspects, and as described above, the textual information within each of the detected zones may have a corresponding logical role and/or purpose within a document or object associated with the captured image data.

By way of example, apparatus 110 may capture an image of a train schedule for a local rail station that includes, among other things, information identifying arriving trains, departing trains, and various general announcements. In some embodiments, processor 540 may execute image processing module 604 to identify portions of the captured image data that include textual information, and further, may execute zone detection module 608 to detect zones of the identified textual information that inform the user of apparatus 110 of the arriving trains, the departing trains, and the general announcements. In additional embodiments, processor 540 may execute zone detection module 608 in conjunction with OCR module 606 to detect one or more zones within the textual information, and to subsequently identify and retrieve machine-readable text from the textual information disposed within the zones.

Referring back to FIG. 6, memory 520 may also be configured to store a contextual data identification module 610, a contextual information database 624, and a contextual rule database 626. In an embodiment, processor 540 may, upon execution of contextual data identification module 610, access contextual information database 624 and obtain contextual information having a direct or indirect relationship with the identified textual information and/or the captured image data. By way of example, contextual information consistent with the disclosed embodiments may include, but is not limited to, a time or a location at which apparatus 110 captured a portion of the textual information, information identifying a specific document or type of document associated with captured image data (e.g., a newspaper, magazine, or web page), information indicative of one or more user preferences for an audible presentation of textual information, a location of a user, demographic information associated with the user, and any additional or alternate contextual information appropriate to the user, the textual information, and apparatus 110.

Further, processor 540 may also access contextual rule database 626 upon execution of contextual data identification module 610, and may obtain one or more contextual rules that associate elements of the contextual information with corresponding portions of textual information within the captured image data. In some aspects, the contextual rules may associate an element of contextual information with one or more of the portions that should be excluded from an audible presentation. Additionally or alternatively, the contextual rules may associate elements of the contextual information with one or more of the portions that should be included within the audible presentation. Further, in other embodiments, the contextual rules may identify an order in which processor 540 presents the portions to the user during the audible presentation, and/or may specify that processor 540 should prioritize one or more of the portions during the audible presentation.

As illustrated in FIG. 6, memory 520 may also be configured to store a text analysis module 612 and an audible representation generation module 614. In one embodiment, processor 540 may execute text analysis module 614 to identify portions of the textual information for audible presentation to the user. In certain aspects, upon execution of text analysis module, processor 540 may leverage contextual information associated with the captured image data and one or more corresponding contextual rules to identify portions of the textual information that should be included within an audible presentation. As described above, the identified portions of textual information may include portions of machine-readable text identified and retrieved using a corresponding OCR process, and further, may also include textual information disposed within corresponding zones having specific logical roles or purposes within a document or object associated with the captured image data.

In certain aspects, processor 540 may leverage the contextual information and corresponding contextual rules to identify at least one first portion of the textual information for inclusion in an audible presentation of the textual information, and at least one second portion of the textual information to be excluded from the audible presentation. By way of example, the excluded second portion may include at least one pre-defined word, one or more pre-defined types of textual information (e.g., an author of the textual information, a page number, and/or a publication date). Further, in other aspects, the included first portion and the excluded second portion may be drawn from a single linguistic element of the textual information (e.g., a single sentence or a single paragraph).

In an embodiment, and upon execution of audible representation generation module 614, processor 540 may generate the audible representation of the textual information, which apparatus 110 may present to the user through a speaker or a bone conduction headphone associated with processing unit 140. In some aspects, processor 540 may generate discrete audible representations corresponding to one or more portions of textual information selected for audible presentation (e.g., in accordance with contextual information and corresponding contextual rules), and may concatenate, combine, or order the discrete audible presentations to generate the audible representation of the textual information. For example, as described above, the generated audible representation of the textual information may include the at least one first portion of the textual information, and exclude the at least one second portion of the textual information.

In some aspects, processor 540 may generate and cause apparatus 110 to present the audible representation of the textual information in response to an existence of a "trigger" within the captured image data. By way of example, triggers consistent with the disclosed embodiments include, but are not limited to, an image of a human appendage (e.g., a finger) within the captured image data, an image of a cane or other pointer, or a particular movement of a human appendage, cane, or other pointer within the field-of-view of sensor unit 120. In such instances, processor 540 may detect the existence of the trigger within the captured image data, and may execute audible representation generation module 614 in response to the detected trigger.

In other embodiments, processor 540 may execute audible representation generation module 614 in response to an audible input provided by the user (e.g., an audible input spoken by the user into a microphone associated with apparatus 110), a tactile input provided by the user (e.g., the user may tap a sensor or other input device disposed on a surface of apparatus 110). Further, in some embodiments, processor 540 may execute audible representation generation module

614 automatically upon receipt of the captured image data, or within a predetermined time period after receipt of the captured image data.

Further, in certain embodiments, apparatus 110 may selectively pause and restart the audible presentation of the textual information in response to one or more pre-determined actions by the user. For example, and as described above, processor 540 may execute audible representation generation module 614 to generate the audible representation of the textual information, which apparatus 110 may present to the user. During presentation of the audible representation, sensory unit 120 may continue to capture image data within a corresponding field-of-view of sensory unit 120, and may continuously provide the captured image data to processing unit 140 for storage within image database 622.

In one aspect, and upon execution of audible representation generation module 614, processor 540 may monitor the newly-received captured image data to determine whether the user looks away from the textual information (e.g., through a corresponding change in the field-of-view of sensory unit 120). If processor 540 determines that the user no longer views at least a portion of the textual information, processor 540 may pause the audible presentation and identify a stopping point within the textual information. In certain embodiments, processor 540 may continue to monitor the captured image data to determine whether the user again views at least a portion of the textual information. If the user again views the presented textual information, processor 540 may cause apparatus 110 to present the audible representation of the textual information from the identified stopping point.

In other embodiments, image database 622, contextual information data 624, and/or contextual rule database 626 may be located remotely from memory 520, and be accessible to other components of apparatus 110 (e.g., processing unit 140) via one or more wireless connections (e.g., a wireless network). While three databases are shown, it should be understood that one or more of image database 622, contextual information data 624, and contextual rule database 626 may be combined and/or interconnected databases may make up the databases. Image database 622, contextual information data 624, and/or contextual rule database 626 may further include computing components (e.g., database management system, database server, etc.) configured to receive and process requests for data stored in associated memory devices.

Figure 7:
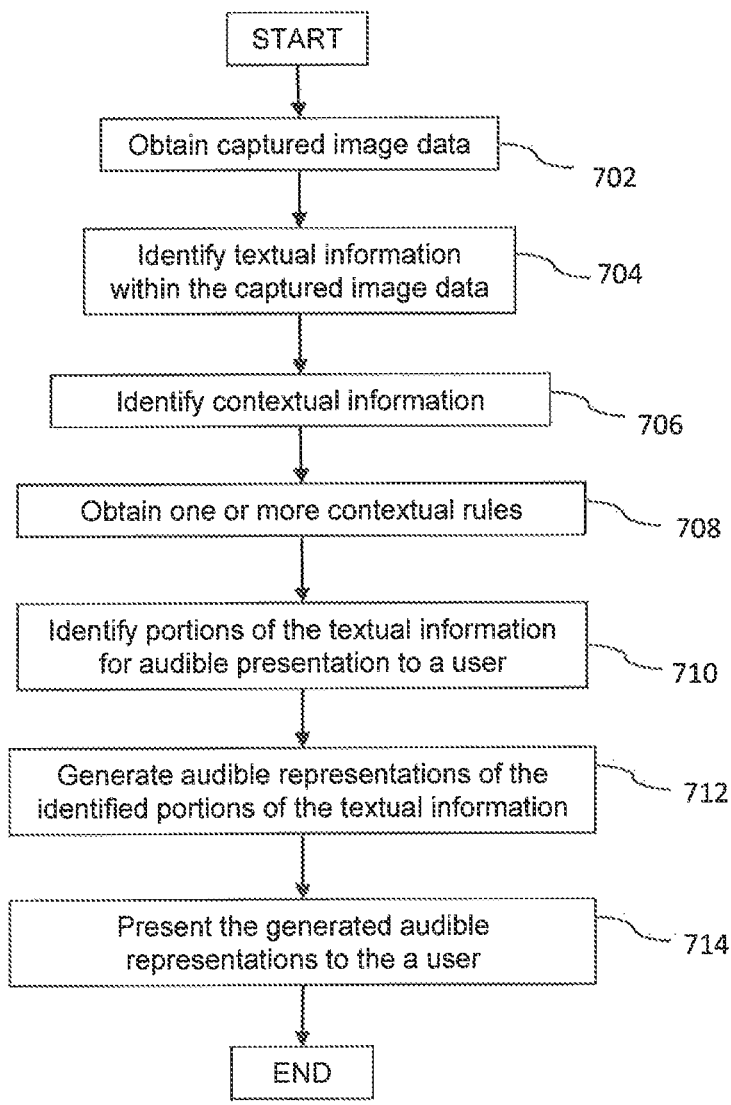
FIG. 7 is a flow diagram of an exemplary process audibly presenting textual information disposed within captured image data, according to disclosed embodiments.

Image data storage module 602, image processing module 604. OCR module 606, zone detection module 608, contextual data identification module 610, text analysis module 612, and audible representation generation module 614 may be implemented in software, hardware, firmware, a mix of any of those, or the like. For example, if the modules are implemented in software, they may be stored in memory 520, as shown in FIG. 6. Other components of processing unit 140 and/or sensory unit 120 may be configured to perform processes to implement and facilitate operations of the modules. Thus, image data storage module 602, image processing module 604. OCR module 606, zone detection module 608, contextual data identification module 610, text analysis module 612, and audible representation generation module 614 may include software, hardware, or firmware instructions (or a combination thereof) executable by one or more processors (e.g., processor 540), alone or in various combinations with each other. For example, the modules may be configured to interact with each other and/or other modules of apparatus 110 to perform functions consistent with disclosed embodiments. In some embodiments, any of the disclosed modules (e.g., image data storage module 602, image processing module 604. OCR module 606, zone detection module 608, contextual data identification module 610, text analysis module 612, and audible representation generation module 614) may each include dedicated sensors (e.g., IR, image sensors, etc.) and/or dedicated application processing devices to perform the functionality associated with each module, FIG. 7 is a flow diagram of an exemplary process 700 for generating audible representations of textual data within captured image data, in accordance with disclosed embodiments. As described above, sensory unit 120 may capture image data that includes textual information and non-textual information disposed within a corresponding field-of-view. Processing unit 130 may receive the captured image data, and processor 540 may execute one or more application modules to identify portions of textual information for audible presentation based on contextual information and one or more corresponding contextual rules. Process 700 provides further details on how processor 540 identifies portions of textual information for audible representation based on contextual information and contextual rules that associate elements of the contextual information with corresponding ones of the portions.

In step 702, processor 540 may obtain captured image data. In some aspects, sensory unit 120 may capture one or more images, and the captured image data may be transmitted to processing unit 140 across wired or wireless communications link 130. Processor 540 may, in step 702, obtain the captured image data directly from sensory module 120 across communications link 130, or alternatively, processor 540 may retrieve the captured image data from a corresponding data repository (e.g., image database 622 of memory 540). By way of example, the captured image data may include one or more regions of printed, displayed, or projected information.

In step 704, processor 540 may analyze the captured image data to identify textual information. As described above, the textual information may include, but is not limited to, printed, handwritten, projected, coded, or displayed text, and processor 540 may perform a layout analysis to detect the textual information within the captured image data. By way of example, the detected textual information may include, but are not limited to, paragraphs of text, blocks of text, regions that include text, logos, titles, captions, footnotes, and any additional or alternate portions of the captured image data that includes printed, handwritten, displayed, coded, and/or projected text.

In step 706, processor 540 may identify contextual information associated with the identified textual data and/or the captured image. By way of example, in step 706, processor 540 may access a corresponding data repository (e.g., contextual information database 624 of memory 540) to identify and obtain the contextual information. In some aspects, as described above, the contextual information may include any information having a direct or indirect relationship with the identified textual information and/or the captured image data. For example, the contextual information may include, but is not limited to, a time or a location at which apparatus 110 captured a portion of the textual information, information identifying a specific document or type of document associated with captured image data (e.g., a newspaper, magazine, or web page), information indicative of one or more user preferences for an audible presentation of textual information, a location of a user, demographic information associated with the user, and any additional or alternate contextual information appropriate to the user, the textual information, and apparatus 110.

In step 708, processor 540 may obtain one or more contextual rules associated with the identified contextual information. By way of example, in step 708, processor 540 may access a corresponding data repository (e.g., contextual rules database 626) to identify and obtain the one or more contextual rules. In some aspects, at least one of the contextual rules may associate an element of the contextual information with a corresponding portion of the textual information that should be excluded from an audible presentation of the textual information. In other aspects, at least one of the contextual rules may associate an element of the contextual information with a corresponding portion of the textual information that should be included within the audible presentation. Additionally or alternatively, the contextual rules may specify a order in which processor 540 should audibly present corresponding portions of the textual information, and further may specify that one or more portions the textual information are prioritized during the audible presentation.

In step 710, processor 540 may leverage the contextual information and the contextual rules to identify portions of the textual information that should be included within the audible presentation of the textual information. As described above, processor 540 may identify portions of textual information in step 710 that include portions of machine-readable text identified and retrieved using a corresponding OCR process. Further, in some aspects, processor 540 may identify portions of the textual information disclosed within at least one zone having a specific logical role or purpose within a document or object associated with the captured image data.

In one embodiment, in step 710, processor 540 may leverage the contextual information and corresponding contextual rules to identify at least one first portion of the textual information for inclusion in the audible presentation, and at least one second portion of the textual information to be excluded from the audible presentation. By way of example, the excluded second portion may include at least one pre-defined word, one or more pre-defined types of textual information (e.g., an author of the textual information, a page number, and/or a publication date). Further, in other aspects, the included first portion and the excluded second portion may be drawn from a single linguistic element of the textual information (e.g., a single sentence or a single paragraph).

In step 712, processor 540 may generate audible representations of the one or more identified portions of the textual information (e.g., the portions identified in step 710), and in step 714, processor 540 may configure apparatus 110 to present the generated audible representations to the user through a speaker or a bone conduction headphone associated with processing unit 140. In one embodiment, processor 540 may order (e.g., as specified within a corresponding one of the contextual rules), concatenate, or otherwise combine the generated audible representation to form a collective audible representation of the textual information within the captured data, which may be present to the user of apparatus 110 in step 714.

By way of example, as described above in reference to step 710, processor 540 may identify a first portion of the textual information that will be included within the audible representation of the textual information, and further, may identify a second portion of the textual information that will be excluded from the audible presentation. In such an instance, processor 540 may generate an audible representation of the first portion of the textual information in step 712, and may cause apparatus 110 to present the generated audible representation to the user in step 714. Upon presentation of the audible representation of the textual information to the user, exemplary routine 700 is complete.

In some aspects, processor 540 may generate and cause apparatus 110 to present the audible representations in response to an existence of a "trigger" within the captured image data. By way of example, triggers consistent with the disclosed embodiments include, but are not limited to, an image of a human appendage within the captured image data, an image of a cane or other pointer, or a particular movement of a human appendage, cane, or other pointer within the field-of-view of sensor unit 120. In such instances, processor 540 may detect the existence of the trigger within the captured image data, and in response to the detected trigger, may generate the audible representations of the identified portions of the textual information in step 712.

In other embodiments, processor 540 may cause apparatus 110 to present the generated audible representation in response to an audible input provided by the user (e.g., an audible input spoken by the user into a microphone associated with apparatus 110), a tactile input provided by the user (e.g., the user may tap a sensor or other input device disposed on a surface of apparatus 110).

Further, in certain embodiments, apparatus 110 may adaptively pause and restart the audible presentation of the textual document in response to pre-determined actions of the user. For example, and as described above; processor 540 may generate the audible representation of the textual information, which apparatus 110 may present to the user in step 714. During presentation of the audible representation, sensory unit 120 may continue to capture image data within a corresponding field-of-view of sensory unit 120, and may continuously provide the captured image data to processing unit 140 for storage within image database 622.

In one aspect, processor 540 may monitor the newly-received captured image data to determine whether the user glances away from the textual information (e.g., through a corresponding change in the field-of-view of sensory unit 120). If processor 540 determines that the user no longer views at least a portion of the textual information, processor 540 may cause apparatus 110 to pause the audible presentation of the textual information in step 714, and may identify a stopping point within the textual information that corresponds to the paused audible presentation. In certain embodiments, processor 540 may continue to monitor the captured image data to determine whether the user again views at least a portion of the textual information. If the user again views the textual information, processor 540 may cause apparatus 110 to re-start a presentation of the audible representation from the identified stopping point.

Using the embodiments described above, processor 540 may identify textual information within captured image data (e.g., step 704 of FIG. 7), identify and obtain contextual information and corresponding contextual rules (e.g., steps 706 and 708 of FIG. 7), and identify one or more portions of the textual information for audible presentation based on the contextual information and the corresponding contextual rules (e.g., step 710 of FIG. 7). In some embodiments, described below in reference to FIG. 8, processor 540 may identify at least one of the textual information portions based on an analysis of machine-readable text retrieved from the textual information by a corresponding OCR process.

Figure 8:
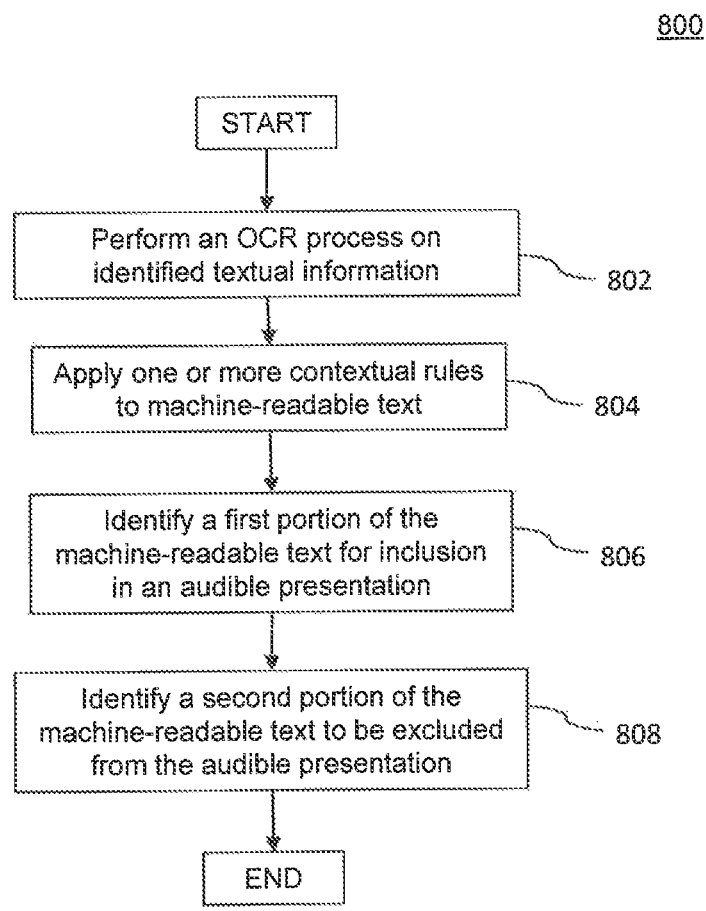
FIG. 8 is a flow diagram of an exemplary process for identifying portions of machine-readable text for audible presentation, according to disclosed embodiments.

FIG. 8 is a flow diagram of an exemplary process 800 that identifies portions of machine-readable text for audible presentation to a user, according to disclosed embodiments. As described above, processor 540 may leverage contextual information and corresponding contextual rules to identify a first portion of textual information to be included within an audible representation of the textual information, and further, a second portion of the textual information to be excluded from the audible representation. In some embodiments, the first and second portions of the textual information may include machine-readable text retrieved from the textual information through a corresponding OCR process. Process 800 provides further details on how processor 540 performs an OCR process to retrieved machine-readable text from textual information within captured image data, and leverages contextual information and one or more contextual rules to identify portions of the machine-readable text for audible presentation to a user.

In step 802, processor 540 may perform an OCR process on at least a portion of textual information included within captured image data to identify and retrieve machine-readable text. As described above, sensory unit 120 may capture one or ore images, and the captured image data may be transmitted to processing unit 140 across wired or wireless communications link 130. Processor 540 may obtain the captured image data (e.g., step 702 of FIG. 7) and may analyze the captured image data to identify portions of the captured image data that include the textual information (e.g., step 704 of FIG. 7). By way of example, the textual information may include, but is not limited to, paragraphs of text, blocks of text, regions that include text, logos, titles, captions, footnotes, and any additional or alternate portions of the image data that includes printed, handwritten, displayed, coded, and/or projected text.

In step 804, processor 540 may apply one or ore contextual rules to the retrieved machine-readable text. In certain aspects, at least one of the contextual rules may associate contextual information with a specific portion of the machine-readable text that will be excluded from an audible presentation of the textual information. Additionally or alternatively, at least one of the contextual rules may associate the contextual information with a specific portion of the machine-readable text that will be included within the audible presentation. Further, in additional aspects, contextual rules consistent with the disclosed embodiments may specify an order in which processor 540 may audibly present specific portions of the machine-readable text to the user. By way of example, the specified ordering may prioritize one or more portions of the machine-readable text that may be of particular importance to the user, such as information relevant to the user's health, safety, and well-being (e.g., portions of machine-readable text within a menu that correspond to an allergy of the user).

In some aspects, as described above, processor 540 may obtain the contextual information and the contextual rules from corresponding data repositories (e.g., contextual information database 624 and contextual rules database 626 of memory 520). As described above, the contextual information may include any information having a direct or indirect relationship with the textual information. For example, the obtained contextual information may include, but is not limited to, a time or a location at which apparatus 110 captured a portion of the textual information, information identifying a specific document or type of document associated with captured image data (e.g., a newspaper, magazine, or web page), information indicative of one or more user preferences for an audible presentation of textual information, a location of a user, demographic information associated with the user, and any additional or alternate contextual information appropriate to the user, the textual information, and apparatus 110.

In step 808, processor 540 may identify at least one first portion of the machine-readable text that will be included within the audible representation, and in step 808, processor 540 may identify at least one second portion of the machine readable text that will be excluded from the audible representation. As described above, processor 540 may identify the first and second portions based on an application of one or more contextual rules to the machine-readable text.

In certain aspects, in step 808, processor 540 may identify a plurality of first portions of the machine-readable text for inclusion within the audible presentation, and further, may identify an order in which the audible representation presents the identified first portions to the user. Additionally, in some aspects, the excluded second portion may include at least one pre-defined word or pre-defined types of machine-readable text (e.g., an author of the textual information, a page number, and/or a publication date). Further, in other aspects, the included first portion and the excluded second portion may be drawn from a single sentence or a single paragraph within the machine-readable text.

Upon identification of the first and second portions of the machine-readable text, exemplary process 800 is complete. In certain embodiments, processor 540 may then generate an audible representation of the first portions of the machine-readable text and cause apparatus 110 to present the generated audible representation to the user, as described above in reference to steps 712 and 714 of FIG. 7.

Using the embodiments described above, apparatus 110 may capture image data that includes textual information, perform an OCR process to identify and retrieve machine-readable text from the textual information, and present, to a user, audible representations of portions of the machine-readable text selected in accordance with one or more contextual rules. By way of example, as illustrated in FIG. 9, a user of apparatus 110 may view a page 900 of a printed newspaper, and apparatus 110 may capture an image that includes a portion 902 of page 900 corresponding to a field-of-view of sensory unit 120.

As described above, processor 540 may identify textual information within the captured image data (e.g., step 704 of FIG. 7), may identify contextual information associated with the captured image data (e.g., step 706 of FIG. 7), may obtain one or more contextual rules associated with the contextual information (e.g., step 708 of FIG. 7), and further, may perform an OCR process on the textual information to identify and retrieve machine-readable text (e.g., step 802 of FIG. 8). By way of example, processor 540 may obtain contextual information identifying a type of document associated with the captured image data (e.g., a printed newspaper article), and obtain a contextual rule indicating that processor 540 should exclude an author, the publication date, and a page number from an audible presentation of a printed newspaper article.

Figure 9:
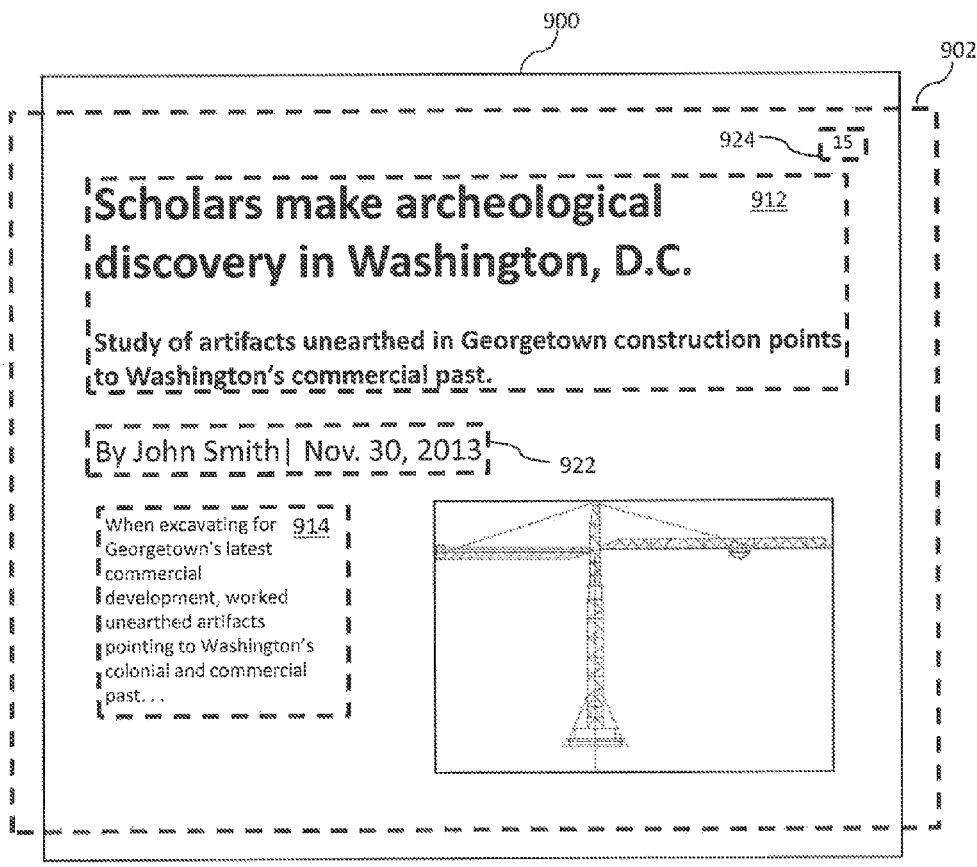
FIGS. 9 and 10 illustrate exemplary image data captured by an apparatus for aiding persons who have low vision, according to disclosed embodiments.

As illustrated in FIG. 9, processor 540 may apply the obtained contextual rule to the retrieved machine-readable text of the printed newspaper article to select text portion 912 (e.g., a title of the printed newspaper article) and text portion 914 (e.g., a body of the printed newspaper article) for inclusion within an audible representation of the printed newspaper article. Further, processor 540 may determine that text portion 922 (e.g., an author and publication date of the printed newspaper article) and text portion 924 (e.g., a page number of the printed newspaper article) should be excluded from the audible representation. As described above processor 540 may then generate the audible representation of text portions 912 and 914, and cause processor 540 to present the generated audible representation to a user through a speaker or a bone conduction headphone.

The disclosed embodiments are, however, not limited to contextual information that identifies to a type of a document associated with the captured image data. In additional embodiments, as described above, processor 540 may obtain contextual information that identifies not only the document type, but also one or more user preferences for an audible presentation of textual information disposed within the captured image data. By way of example, as illustrated in FIG. 10, a user of apparatus 110 view a printed menu 1000 provided by a restaurant, and apparatus 110 may capture an image that includes a portion 1002 of menu 1000 corresponding to a field-of-view of sensory unit 120.

As described above, processor 540 may identify textual information within the captured image data (e.g., step 704 of FIG. 7), may identify contextual information associated with the captured image data (e.g., step 706 of FIG. 7), may obtain one or more contextual rules associated with the contextual information (e.g., step 708 of FIG. 7), and further, may perform an OCR process on the textual information to identify and retrieve machine-readable text (e.g., step 802 of FIG. 8). In certain aspects, processor 540 may obtain contextual information that identifies a type of document associated with the captured image data (e.g., a menu) and one or more user preferences for an audible presentation of textual information disposed within the menu. By way of example, the user preferences within the contextual information may indicate that the user prefers an audible presentation of "vegetarian" and "vegan" items on the menu. In certain aspects, processor 540 may obtain a contextual rule indicating that processor 540 should generate audible representations of textual information corresponding to "vegan" or "vegetarian" items within menu 1000.

Figure 10:
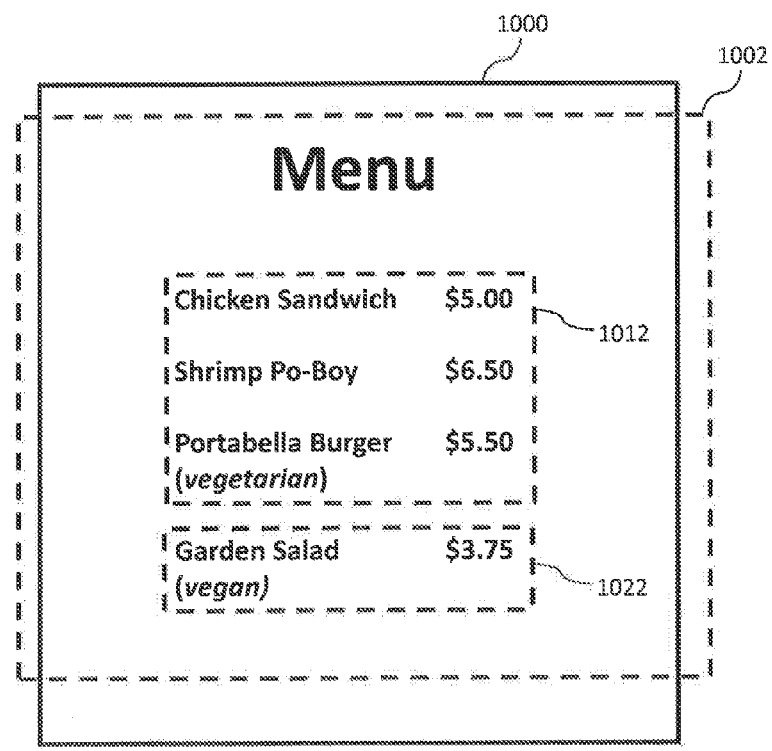

As illustrated in FIG. 10, processor 540 may apply the obtained contextual rule to the retrieved machine-readable text of menu 1000 to select text portion 1022, which corresponds to a "garden salad" identified as "vegan," for inclusion within an audible representation of menu 1000. Further, based on an application of the obtained contextual rule to the machine-readable text, processor 540 may determine that text portion 1012, which corresponds to various non-vegan and non-vegetarian menu items, should be excluded from the audible representation. As described above processor 540 may then generate the audible representation of text portion 1022, and cause processor 540 to present the generated audible representation to a user through a speaker or a bone conduction headphone.

In the embodiments described above, processor 540 may perform an OCR process that retrieves machine-readable text from textual information within captured image data, and may identify portions of the machine-readable text for audible presentation to a user based on an application of one or more contextual rules. In additional embodiments, processor 540 may leverage a logical structure of the textual information to identify portions of the textual information that should be audibly presented to the user. For example, as described below in reference to FIG. 11, the textual information within captured image data may be disposed into one or more "zones" having corresponding logical roles or purposes within a document or object associated with the captured image data. In certain aspects, processor 540 may identify portions of the textual information for audible presentation based on the application of the contextual rules to the textual information within the corresponding zones.

Figure 11:
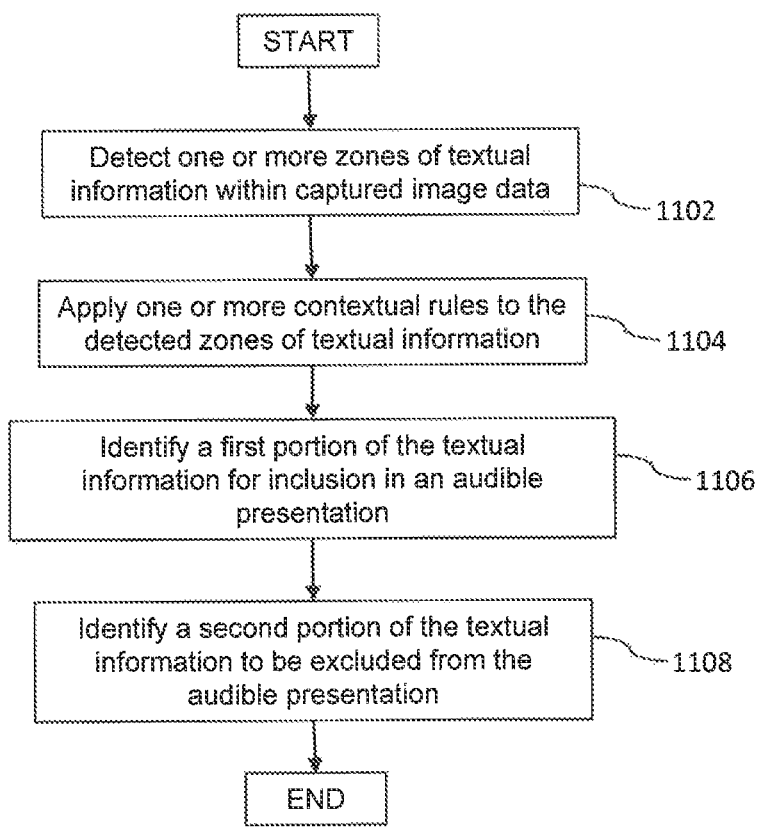
FIG. 11 is a flow diagram of an exemplary process for identifying portions of textual information for audible presentation based on a logical structure of the textual information, according to disclosed embodiments.

FIG. 11 is a flow diagram of an exemplary process 1100 that identifies portions of textual information for audible presentation based on a logical structure of the textual information, according to disclosed embodiments. As described above, processor 540 may leverage contextual information and corresponding contextual rules to identify a first portion of textual information suitable for inclusion within an audible representation of the textual information, and further, a second portion of the textual information to be excluded from the audible representation. In some embodiments, the first and second portions may include textual information disposed within one or more zones having corresponding logical roles or purposes within a document or object associated within the captured image data. Process 1100 provides further details on how processor 540 performs a process that detects one or more zones of textual information within captured image data, and applies one or more contextual rules to the detected zones to identified portions of textual information for audible presentation.

In step 1102, processor 540 may analyze the textual information to detect a presence of one or more zones having corresponding roles or purposes. As described above, sensory unit 120 may capture one or more images, and the captured image data may be transmitted to processing unit 140 across wired or wireless communications link 130. Processor 540 may obtain the captured image data (e.g., step 702 of FIG. 7) and may analyze the captured image data to identify portions of the captured image data that include the textual information (e.g., step 704 of FIG. 7). By way of example, the textual information may include, but are not limited to, paragraphs of text, blocks of text, regions that include text, logos, titles, captions, footnotes, and any additional or alternate portions of the image data that includes printed, handwritten, displayed, coded, and/or projected text.

Further, in some aspects, the logical roles or purposes that correspond to the detected zones may be defined based on an object or type of object captured within the image data. For example, the image data may capture a train schedule disposed within a field-of-view of apparatus 110, and the captured image data may include textual information disposed into discrete zones that inform a user of apparatus 110 of scheduled departures, scheduled arrivals, and messages provided to passengers by a corresponding railway carrier. Further, the textual information disposed within corresponding ones of the detected zones may include, but is not limited to, words, phrases, sentences, or other structured strings of alphanumeric characters having a logical roles or purposes consistent with the corresponding detected zone.

In step 1104, processor 540 may apply one or more contextual rules to the textual information disposed within the detected zones. In certain aspects, at least one of the contextual rules may associate contextual information with a specific portion of the textual information that will be excluded from an audible presentation of the textual information. Additionally or alternatively, at least one of the contextual rules may associate the contextual information with a specific portion of the textual information that will be included within the audible presentation. Further, in additional aspects, contextual rules consistent with the disclosed embodiments may specify an order in which processor 540 may audibly present specific portions of the textual information to the user. By way of example, the specified ordering may prioritize one or more portions of the textual information that may be of particular importance to the user, such as information relevant to the user's health, safety, and well-being (e.g., processor 540 may prioritize an audible presentation of portions of textual information relevant to an allergy of the user).

In some aspects, as described above, processor 540 may obtain the contextual information and the contextual rules from corresponding data repositories (e.g., contextual information database 624 and contextual rules database 626 of memory 520), and the contextual information may include any information having a direct or indirect relationship with the textual information. For example, the obtained contextual information may include, but is not limited to, a time or a location at which apparatus 110 captured a portion of the textual information, information identifying a specific document or type of document associated with captured image data (e.g., a newspaper, magazine, or web page), information indicative of one or more user preferences for an audible presentation of textual information, a location of a user, demographic information associated with the user, and any additional or alternate contextual information appropriate to the user, the textual information, and apparatus 110.

In step 1106, processor 540 may identify a first portion of the textual information that should be included within the audible representation, and in step 1108, processor 540 may identify at least one second portion of the machine readable text that will be excluded from the audible representation. In one embodiment, the identified first and second portion may include textual information disposed within one or more of the detected zones, and processor 540 may identify the first and second portions based on an application of one or more contextual rules to the textual information disposed within the detected zones. Further, in additional embodiments, processor 540 may perform an OCR process on the textual information within the detected zones to facilitate the identification of the first and second portions of the textual information.

Upon identification of the first and second portions of the machine-readable text, exemplary process 1100 is complete. In certain embodiments, processor 540 may then generate an audible representation of the first portions of the machine-readable text and cause apparatus 110 to present the generated audible representation to the user, as described above in reference to steps 712 and 714 of FIG. 7.

As described above in reference to FIG. 11, apparatus 110 may capture image data that includes textual information (e.g., step 702 of FIG. 7), analyze the textual information to detect one or more zones into which the textual information is disposed (e.g., step 1102 of FIG. 11), apply one or more contextual rules to the detected zones of textual information (e.g., step 1104 of FIG. 11), and identify portions of textual information disposed within at least one of the detected zones for audible presentation to a user (e.g., steps 1106 and 1108 of FIG. 11). By way of example, as illustrated in FIG. 12, a user of apparatus 110 view a printed train schedule 1200, and apparatus 110 may capture an image that includes a portion 1202 of schedule 1200 corresponding to a field-of-view of sensory unit 120.

Figure 12:
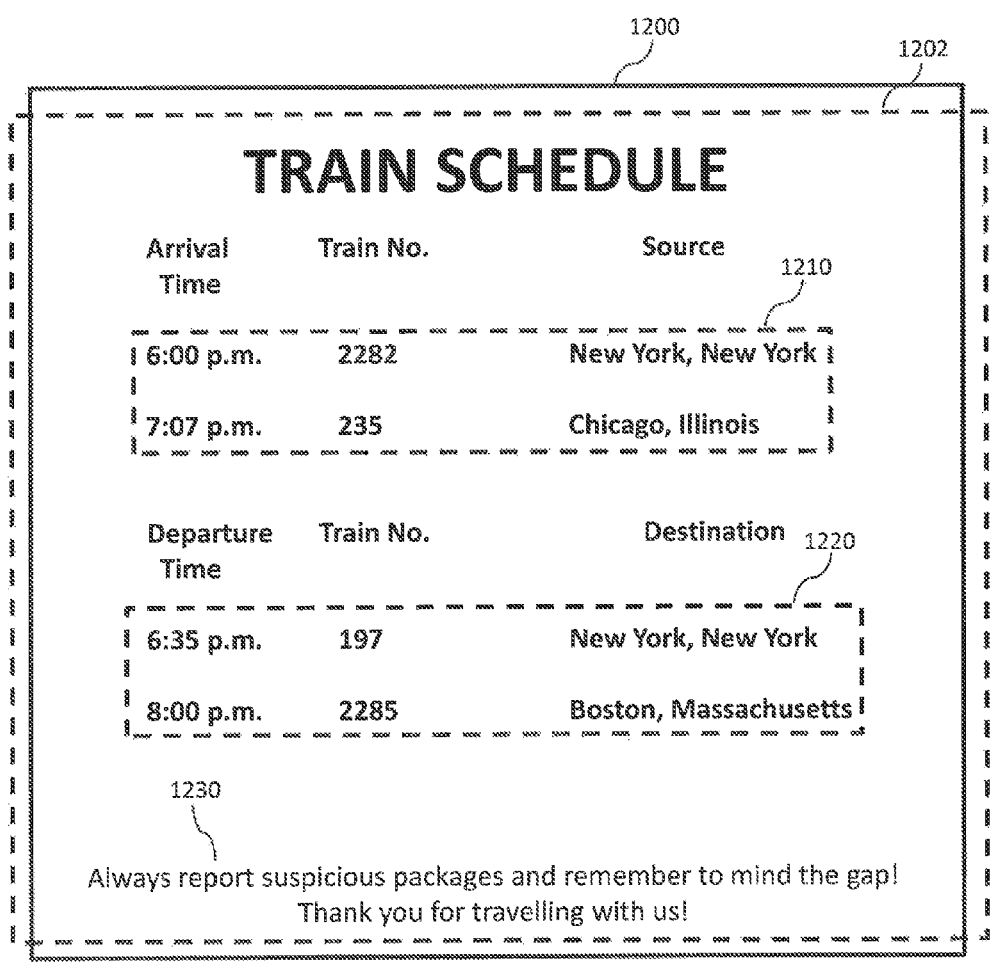
FIG. 12 illustrates exemplary image data captured by an apparatus for aiding persons who have low vision, according to disclosed embodiments.

For example, in FIG. 12, processor 540 may detect within schedule 1200 a first zone 1210 that informs a user of one or more arriving trains, a second zone 1220 that informs the user of one or more departing trains, and a third zone 1230 that provides one or more general announcements to the user. In certain aspects, processor 540 obtain one or more contextual rules that explicitly exclude zones of a train schedule that inform the user of arriving trains and general announcements from a corresponding audible presentation. In such an instance, processor 540 may apply the obtained contextual rule to the detected zones of schedule 1200 to select textual information disposed within second zone 1220 (e.g., which informs the user of departing trains) for inclusion within an audible representation of schedule 1200. Further, processor 540 may determine that first and third zones 1210 and 1230 (which respectively inform the user of arriving trains and general announcements) should be excluded from the audible representation. As described above processor 540 may then generate the audible representation of the textual information within first zone 1220, and cause processor 540 to present the generated audible representation to a user through a speaker or a bone conduction headphone.

In additional embodiments, the exemplary processes of FIGS. 8 and 11 may be leveraged collectively to identify portions of textual information for audible presentation that better conform to the needs and preferences of a user of apparatus 110. In certain aspects, processor 540 may perform an OCR process on the textual information disposed within one or more of detected zones (e.g., as detected in step 1102 of FIG. 11) to generate audible representations of textual information that have specific logical roles and conform to specific user preferences.

For example, processor 540 may obtain contextual data that specifies a preference for audible presentations identifying trains that depart within a threshold time period (e.g., thirty minutes) of a time at which a user of apparatus 110 arrives at a train station. Accordingly, in such exemplary embodiments, processor 540 may obtain one or more contextual rules that explicitly exclude zones of a train schedule that inform the user of arriving trains and general announcements from a corresponding audible presentation, and further, that exclude textual information within a zone that informs the user of departing trains from the corresponding audible presentation if that textual information corresponds to a train that departs outside of the threshold time period.

Referring back to FIG. 12, and as described above, processor 540 may apply the obtained contextual rule to the detected zones of schedule 1200 to exclude first and third zones 1210 and 1230 from the audible representation. Further, for example, if the user were to arrive at the train station at 6:08 p.m., processor 540 may determine that textual information within second zone 1220 corresponding to "Train No. 2285" to "Boston, Mass.," should be excluded from the audible presentation because the departure time of "8:00 p.m." falls outside of the threshold time period of thirty minutes. Accordingly, processor 540 may generate an audible representation of a portion of textual information within second zone 1220 corresponding to "Train No. 197" departing at 6:35 p.m. for New York, N.Y., since this textual information is disposed within the specified zone and corresponds to a train departing within the pre-determined threshold time period. As described above, processor 540 may cause apparatus 110 to present the generated audible representation to a user through a speaker or a bone conduction headphone.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks, floppy disks, or CD ROM, or other forms of RAM or ROM, USB media, DVD, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets. One or more of such software sections or modules can be integrated into a computer system or existing e-mail or browser software.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed routines may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A system for audibly presenting text retrieved from a captured image, the system comprising:
   at least one processor device configured to:
      receive at least one image of text to be audibly presented, the text including a first portion and a second portion;
      identify contextual information associated with the text;
      access at least one rule associating the contextual information with at least one portion of text to be excluded from an audible presentation associated with the text;
      perform an analysis on the at least one image to identify the first portion and the second portion; and
      cause the audible presentation, wherein the audible presentation includes the first portion and excludes the second portion.

2. The system of claim 1, wherein the second portion includes at least one of: a name associated with the author of the text, a page number, and a date.

3. The system of claim 1, wherein the second portion includes at least one predefined word.

4. The system of claim 1, wherein the first portion and the second portion are part of a same paragraph.

5. The system of claim 1, wherein the contextual information includes information about a type of object associated with the text.

6. The system of claim 1, wherein the contextual information includes information about a type of document associated with the text.

7. The system of claim 6, wherein the contextual information includes predefined information about preferences of a user associated with the type of document.

8. The system of claim 1, wherein the contextual information includes information indicative of a location of the user.

9. The system of claim 1, wherein the first portion includes a plurality of sub-portions, and the at least one rule further associates the contextual information with a presenting order of the plurality of sub-portions.

10. The system of claim 1, wherein the analysis includes initiating an optical character recognition process and application of the at least one rule to identify the first portion and the second portion in the text.

11. The system of claim 1, wherein the analysis includes detecting different zones in the text, each zone being associated with differing logical roles, and applying the at least one rule to identify the first portion and the second portion in the text.

12. The system of claim 1, wherein the at least one processor device is further configured to initiate an optical character recognition process to recognize at least the first portion.

13. The system of claim 12, wherein the at least one processor device is further configured to recognize characters defined by 10 or less pixels.

14. The system of claim 12, wherein the at least one processor device is further configured to recognize characters defined by 6 or less pixels.

15. An apparatus for audibly presenting text retrieved from a captured image, the apparatus comprising;
   an image sensor configured to capture images from an environment of a user;
   at least one processor device configured to:
      receive at least one image of text to be audibly presented, the text including a first portion and a second portion;
      identify contextual information associated with the text;
      access at least one rule associating the contextual information with at least one portion of text to be excluded from an audible presentation associated with the text;
      perform an analysis on the at least one image to identify the first portion and the second portion; and
      cause the audible presentation, wherein the audible presentation includes the first portion and excludes second portion.

16. The apparatus of claim 15, wherein the image sensor is further configured to be connected to glasses worn by the user to enable the image sensor to move with a head of the user.

17. The apparatus of claim 15, wherein the image sensor is further configured to be movable with a head of the user and an aiming direction of the image sensor substantially coincides with a field of view of the user.

18. The apparatus of claim 15, wherein the at least one processor device is further configured to automatically stop the audible presentation when the user looks away from the text.

19. The apparatus of claim 18, wherein the at least one processor device is further configured to automatically resume the audible presentation when the user looks back at the text.

20. The apparatus of claim 18, wherein the at least one processor device is further configured to resume the audible presentation from a previous stopping point when the user looks back at the text.

21. The apparatus of claim 15, wherein the at least one processor device is further configured to determine an existence of a trigger in the at least one image, the trigger being associated with a desire of the user to hear the text read aloud.

22. A method for audibly presenting text retrieved from a captured image, the method comprising:
   receiving at least one image of text to be audibly presented, the text including a first portion and a second portion;
   identifying contextual information associated with the text;
   accessing at least one rule associating the contextual information with at least one portion of text to be excluded from an audible presentation associated with the text;
   performing an analysis on the at least one image to identify the first portion and the second portion; and
   causing the audible presentation, wherein the audible presentation includes the first portion and excludes second portion.

23. A software product stored on a non-transitory computer readable medium and comprising data and computer implementable instructions for carrying out the method of claim 22.

* * * * *